United States Patent
Sarria Villada et al.

(10) Patent No.: US 11,064,666 B2
(45) Date of Patent: Jul. 20, 2021

(54) QTLS CONFERRING RESISTANCE TO POTYVIRUSES IN WATERMELON

(71) Applicant: RIJK ZWAAN ZAADTEELT EN ZAADHANDEL B.V., De Lier (NL)

(72) Inventors: Emilio Sarria Villada, De Lier (NL); Dorthe Bettina Drager, De Lier (NL); Marc Villevieille, De Lier (NL); Denis Maxime Losdat, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 16/051,981

(22) Filed: Aug. 1, 2018

(65) Prior Publication Data
US 2019/0021271 A1    Jan. 24, 2019

Related U.S. Application Data

(63) Continuation-in-part of application No. PCT/EP2017/052523, filed on Feb. 6, 2017.

(30) Foreign Application Priority Data

Feb. 5, 2016 (WO) ................. PCT/EP2016/052544

(51) Int. Cl.
| | |
|---|---|
| *A01H 5/10* | (2018.01) |
| *A01H 6/34* | (2018.01) |
| *C12Q 1/6895* | (2018.01) |
| *A01H 5/08* | (2018.01) |
| *A01H 1/06* | (2006.01) |
| *A01H 4/00* | (2006.01) |
| *A01H 1/02* | (2006.01) |
| *A01H 1/04* | (2006.01) |

(52) U.S. Cl.
CPC ................. *A01H 5/10* (2013.01); *A01H 1/06* (2013.01); *A01H 4/008* (2013.01); *A01H 5/08* (2013.01); *A01H 6/342* (2018.05); *C12Q 1/6895* (2013.01); *A01H 1/02* (2013.01); *A01H 1/04* (2013.01); *C12Q 2600/13* (2013.01); *C12Q 2600/156* (2013.01)

(58) Field of Classification Search
None
See application file for complete search history.

(56) References Cited

PUBLICATIONS

N. Guner, et al., Overview of Polyvirus Resistance in Watermelon, May 17, 2008, Retrieved from the Internet: URL: https://w3.avignon.inra.fr/dspace/bits tream/2174/245/1/30 39 Wehner.pdf [retrieved on Jul. 11, 2014].
Karen R. Harris, et al., Identification and Utility of Markers Linked to the Zucchini Yellow Mosaic Virus Resistance Gene in Watermelon, Journal of The American Society for Horticultural Science (2009) vol. 134(5):529-534.
Kai-Shu Ling, et al., Non-synonymous Single Nucleotide Polymorphisms in the Watermelon eIF4E Gene are Closely Associated with Resistance to Zucchini Yellow Mosaic Virus, Theoretical and Applied Genetics: International Journal of Plant Breeding Research (Oct. 10, 2009) vol. 120, No. 1, pp. 191-200.
Y. Xu, et al., Inheritance of Resistance to Zucchini Yellow Mosaic Virus and Watermelon Mosaic Virus in Watermelon, Journal of Heredity (Nov. 1, 2004) vol. 95, No. 6, pp. 498-502.
International Search Report and Written Opinion dated May 8, 2017, in Application No. PCT/EP2017/052523.
Wang A, Krishnaswamy S. Eukaryotic translation initiation . . . Mol Plant Pathol. Sep. 2012;13(7):795-803. doi: 10.1111/j.1364-3703.2012.00791.x. Epub Mar. 2, 2012.

*Primary Examiner* — Brent T Page
(74) *Attorney, Agent, or Firm* — Duane Morris LLP; Thomas J. Kowalski; Deborah L. Lu

(57) ABSTRACT

The present invention relates to a watermelon plant showing resistance against potyviruses, wherein the watermelon plant may comprise one or more of resistance conferring alleles of QTL1, QTL2 and QTL3 and wherein the said QTLs are as present in or obtainable from a watermelon plant, representative seed of which was deposited under deposit accession number NCIMB 42537, 42536, 42535 respectively.

13 Claims, 2 Drawing Sheets

Specification includes a Sequence Listing.

QTLS CONFERRING RESISTANCE TO POTYVIRUSES IN WATERMELON

RELATED APPLICATIONS AND INCORPORATION BY REFERENCE

This application is a continuation-in-part application of international patent application Serial No. PCT/EP2017/052523 filed Feb. 6, 2017, which published as PCT Publication No. WO 2017/134297 on Aug. 10, 2017, which claims benefit of European patent application Serial No. PCT/EP2017/052544 filed Feb. 5, 2016.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing, which has been submitted electronically in ASCII format and is hereby incorporated by reference in its entirety.

FIELD OF THE INVENTION

The invention relates to a watermelon plant that is resistant to potyviruses. It furthermore relates to seed and propagation material that can be derived from said watermelon plant or is capable of growing into such watermelon plant. The invention further relates to a marker for selecting a watermelon plant with resistance to potyviruses, a method for selecting said watermelon, and the use of a marker to identify a watermelon plant with resistance to potyviruses.

BACKGROUND OF THE INVENTION

Watermelon plants are grown in large parts of the world. The Southern part of the USA, the Middle East, Africa, India, Japan and Southern Europe are the most important watermelon producing areas. Watermelon is indigenous of tropical Africa, occurring naturally in South Africa, Namibia, Botswana, Zimbabwe, Mozambique, Zambia and Malawi, but is nowadays widely distributed in the whole of Africa and throughout Asia. It is cultivated and adventitious in tropical and subtropical areas of the world. Watermelon is thought to have been domesticated at least 4,000 years ago. Its cultivation dates back to ancient Egypt and India and then spread from there to other countries and regions.

Watermelon belongs to the genus *Citrullus* which is part of the Cucurbit family (Cucurbitaceae). The modern cultivated watermelon is known as *Citrullus lanatus* subsp. *lanatus* (Thunb.), although in literature sometimes the old indication *Citrullus vulgaris* Schrad. is still used.

Potyvirus is a genus of viruses, which is part of the family of the so-called Potyviridae. The name was taken from the type virus in this genus; potato virus Y. Potyviruses are a large problem in agriculture and cause significant losses in many crops. They are mainly spread by different species of aphids.

Zucchini Yellow Mosaic virus, also known as its abbreviated form ZYMV, is a potyvirus, and is a major pathogen of all kinds of cucurbits, like squashes, pumpkins, watermelons, and especially zucchinis as its name indicates. The disease causes symptoms that includes leaf mosaic patterns (hence the name) yellowing of the plant and a so-called shoe-string symptom in the leaves. The fruits can be stunted and deformed, in the worst case the fruits are unmarketable, and the yield seriously reduced.

Another potyvirus that has become a major pathogen in watermelon cultivation is watermelon mosaic virus, known as WMV, and also known under other names: WMV-2 (watermelon mosaic virus type 2), marrow mosaic virus and melon mosaic virus. This virus causes symptoms not only in watermelons, but in most cucurbits, and it could infect probably many other plants from different plant families. The virus is common both in temperate and in tropical regions. The symptoms caused by the virus depend on the host species, the specific virus strain and environmental conditions. The main symptoms are mottling of plant in general and so-called mosaic on the leaves. In watermelon it can cause mosaic lesions and fruit distortion, thus influencing the marketable yield. It has been reported that combinations of WMV and ZYMV with other virus infections could be lethal in watermelon plants.

Both ZYMV and WMV are mainly transmitted by aphids but they can be spread too by interaction with people or tools and machines. The various solutions to control both ZYMV and WMV that have been tried so far, vary from pesticides to reduce the populations of aphids, removing alternative host plants near watermelon fields, to crop rotation.

Citation or identification of any document in this application is not an admission that such document is available as prior art to the present invention.

SUMMARY OF THE INVENTION

In watermelon cultivation there is a need for improved resistance to potyviruses. Furthermore, the inheritance of the existing resistance against potyviruses is still unclear. It is therefore an object of the present invention to provide a watermelon with resistance to potyviruses.

In the research that led to the current invention watermelon plants were developed that are resistant against potyvirus. A QTL mapping study was done to identify the genetic regions responsible for the resistance against potyvirus in the plants of the invention. Three different QTLs (quantitative trait loci) were identified that contribute to potyvirus resistance in the plants of the invention.

The present invention relates to a watermelon plant showing resistance against potyviruses, wherein the watermelon plant may comprise one or more of resistance conferring alleles of QTL1, QTL2 and QTL3 and wherein the said QTLs are as present in or obtainable from a watermelon plant, representative seed of which was deposited under deposit accession number NCIMB 42537, 42536, 42535 respectively. In the seeds of deposit NCIMB 42537 QTL1 is linked to at least one of the marker sequences selected from the group consisting of the even sequence id numbers of SEQ ID NO:4-SEQ ID NO:40. In the seeds of deposit NCIMB 42536 and NCIMB 42538, QTL2 is linked to at least one of the marker sequences selected from the group consisting of the even sequence id numbers of SEQ ID NO:46-SEQ ID NO:86. In the seeds of deposit NCIMB 42535 QTL3 is linked to at least one of the marker sequences selected from the group consisting of the even sequence numbers of SEQ ID NO:92-SEQ ID NO:96.

The invention thus relates to a watermelon plant that may comprise a QTL1 located on chromosome 8, and/or a QTL2 located on chromosome 6, that confer resistance to a potyvirus and wherein QTL1 is as found in a watermelon plant, representative seed of which was deposited under deposit number NCIMB 42537, and wherein in the seeds of the deposit QTL1 is located between molecular markers M2382 and M2386 as defined herein, and wherein QTL2 is as found in a watermelon plant, representative seed of which was deposited under deposit number NCIMB 42536, and wherein in the seeds of the deposit QTL2 is located between molecular markers M2283 and M1567 as defined herein.

The invention further relates to a watermelon plant that may comprise a QTL1 and/or QTL2 and/or may comprise a QTL3 located on chromosome 3, and wherein QTL3 confers resistance to a potyvirus, wherein QTL3 is as found in a watermelon plant, representative seed of which was deposited under deposit accession number NCIMB 42535, and wherein in the seeds of deposit NCIMB 42535 QTL3 is located between molecular markers M2112 and M2122 as defined herein.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U. S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of and" consists essentially of have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Seeds of watermelon *Citrullus lanatus* subsp. *lanatus* that comprise QTL1 in homozygous form that leads to the phenotypic trait of the invention were deposited with NCIMB Ltd, Ferguson Building, Craibstone Estate, Bucksburn, Aberdeen AB21 9YA, UK on Mar. 16, 2002 under deposit accession number NCIMB 42537.

Seeds of watermelon *Citrullus lanatus* subsp. *lanatus* that comprise QTL2 in homozygous form that leads to the phenotypic trait of the invention were deposited with NCIMB Ltd, Ferguson Building, Craibstone Estate, Bucksburn, Aberdeen AB21 9YA, UK on Mar. 2, 2016 under deposit accession number NCIMB 42536.

Seeds of watermelon *Citrullus lanatus* subsp. *lanatus* that comprise QTL3 in homozygous form that leads to the phenotypic trait of the invention were deposited with NCIMB Ltd, Ferguson Building, Craibstone Estate, Bucksburn, Aberdeen AB21 9YA, UK on Mar. 16, 2002 under deposit accession number NCIMB 42535.

Seeds of watermelon *Citrullus lanatus* subsp. *lanatus* that comprise the QTL1 and QTL3 in homozygous form that lead to the phenotypic trait of the invention were deposited with NCIMB Ltd, Ferguson Building, Craibstone Estate, Bucksburn, Aberdeen AB21 9YA, UK on Mar. 2, 2016 under deposit accession number NCIMB 42539.

Seeds of watermelon *Citrullus lanatus* subsp. *lanatus* that comprise the QTL2 and QTL3 in homozygous form that lead to the phenotypic trait of the invention were deposited with NCIMB Ltd, Ferguson Building, Craibstone Estate, Bucksburn, Aberdeen AB21 9YA, UK on Mar. 2, 2016 under deposit accession number NCIMB 42538.

Seeds of watermelon *Citrullus lanatus* subsp. *lanatus* that comprise the QTL1 and QTL2 in homozygous form that lead to the phenotypic trait of the invention, were deposited with NCIMB Ltd, Ferguson Building, Craibstone Estate, Bucksburn, Aberdeen AB21 9YA, UK on Mar. 2, 2016 under deposit accession number NCIMB 42540.

The Deposits with NCIMB Ltd, under deposit accession numbers 42535 to 42540 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
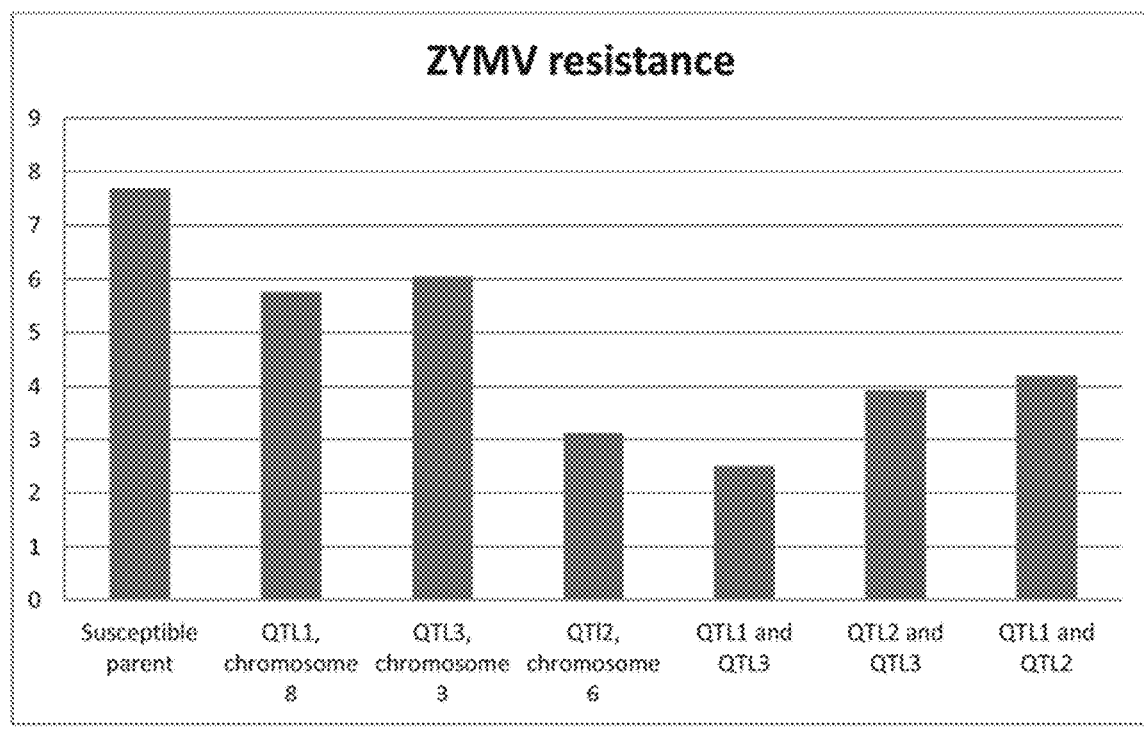
FIG. 1. Graphs showing the differences in ZYMV resistance of watermelon plants which may comprise the potyvirus resistance conferring alleles of QTL1 and/or QTL2 and optionally QTL3, separately or in combination.

A "QTL" or "Quantitative Trait Locus" as used herein is defined as a region (locus) on the genome of the plant that correlates with a specific trait/phenotype, more specifically the variation in the locus is correlated with the variation found in the phenotype. The QTL may comprise gene(s) or is linked to gene(s) that control the trait/phenotype.

The invention thus relates to a watermelon plant that may comprise a QTL1 located on chromosome 8, and/or a QTL2 located on chromosome 6, that confer resistance to a potyvirus and wherein QTL1 is as found in a watermelon plant, representative seed of which was deposited under deposit number NCIMB 42537, and wherein in the seeds of the deposit QTL1 is located between molecular markers M2382 and M2386 as defined herein, and wherein QTL2 is as found in a watermelon plant, representative seed of which was deposited under deposit number NCIMB 42536, and wherein in the seeds of the deposit QTL2 is located between molecular markers M2283 and M1567 as defined herein.

The invention further relates to a watermelon plant that may comprise a QTL1 and/or QTL2 and/or may comprise a QTL3 located on chromosome 3, and wherein QTL3 confers resistance to a potyvirus, wherein QTL3 is as found in a watermelon plant, representative seed of which was deposited under deposit accession number NCIMB 42535, and wherein in the seeds of deposit NCIMB 42535 QTL3 is located between molecular markers M2112 and M2122 as defined herein.

The phrase "invention relates to a watermelon plant that may comprise a QTL1 and/or QTL2 and/or QTL3" also may comprise the situation in which the watermelon plant is resistant to the potyvirus ZYMV and may comprise "QTL1 and/or QTL2 and optionally QTL3". The link between ZYMV resistance and QTL3 (EIF4e gene) in watermelon is already known. Plants of the invention that are resistant to ZYMV thus have in any case either QTL1 or QTL2 or both QTL1 and QTL2 and may also have QTL3. Plants that are resistant to ZYMV and only have QTL3 are not claimed.

A QTL, designated QTL1, was found to be located on watermelon plant chromosome 8, between markers M2382 and M2386. The two forms of the polymorphic marker M2382 are represented by marker sequences SEQ ID NO:1 and SEQ ID NO:2, and the two forms of the polymorphic marker M2386 are represented by marker sequences SEQ ID NO:41 and SEQ ID NO:42, all shown in Table 1. Another QTL, designated as QTL2, was found, located on watermelon plant chromosome 6, between markers M2283 and M1567. The two forms of polymorphic marker M2283 are represented by marker sequence SEQ ID NO:43 and SEQ ID NO:44, and the polymorphic marker M1567 is represented by two marker sequence SEQ ID NO:87 and SEQ ID NO:88, shown in Table 1.

A third QTL, designated as QTL3, was found to be located on chromosome 3, between markers M2112 and M2122. The polymorphic marker M2112 is represented by marker sequence SEQ ID NO:89 and SEQ ID NO:90, shown in Table 1. The polymorphic marker M2122 is represented by marker sequence SEQ ID NO:97 and SEQ ID NO:98, shown in Table 1.

Further research resulted in the mapping of SNPs that can be used for identification of QTL1, QTL2 and/or QTL3.

A "SNP", Single Nucleotide Polymorphism, as used herein is defined as a variation in DNA consisting of a single nucleotide that can differ within a species or a population. They can be the cause of a mutated gene, in this case they are called causal SNP(s) or they can be linked to certain gene appearance/genotypes and can therefore be used as markers.

The term "resistance conferring allele" as used herein is the form of the QTL that causes the potyvirus resistance trait or phenotype.

The SNPs that may be used for identification of QTL1 in a watermelon plant are present in the polymorphic markers M4996, M4997, M4998, M4999, M5000, M5001, M5003, M2384, M5004, M5005, M5007, M5008, M5010, M5011, M5012, M5014, M5015, M5016, and M5017, shown in Table 1.

A polymorphic marker is represented by two possible forms, i.e. marker sequences or marker alleles, that in this case only differ from each other in a single nucleotide polymorphism (SNP). In the seeds of the deposit NCIMB 42537 the resistance conferring allele of QTL1 is linked to the nucleotide that is underlined and bold in a marker sequence selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38 and SEQ ID NO:40, shown in Table 1. The wildtype allele of QTL1 is linked to the nucleotide that is underlined and bold in a marker sequence selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37 and SEQ ID NO:39, shown in Table 1.

In the seeds of deposit NCIMB 42539 and 42540 the resistance conferring allele of QTL1 is linked to the nucleotide that is underlined and bold in a marker sequence selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38 and SEQ ID NO:40, shown in Table 1.

The SNPs that may be used for identification of QTL2 in a watermelon plant are present in polymorphic markers M2285, M4938, M4939, M4940, M4941, M4942, M4943, M4945, M4946, M4947, M4948, M4949, M4950, M4951, M4952, M4953, M2290, M4954, M4955, M4956, and M2296, shown in Table 1.

In the seeds of deposit NCIMB 42536 the resistance conferring allele of QTL2 is linked to the nucleotide underlined and bold in Table 1 in a marker sequence selected from the group consisting of SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, shown in Table 1.

In the seeds of deposit NCIMB 42538 the resistance conferring allele of QTL2 is linked to the nucleotide that is underlined and bold in a marker sequence selected from the group consisting of SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84 and SEQ ID NO:86, shown in Table 1.

In the seeds of deposit NCIMB 42540 the resistance conferring allele of QTL2 is linked to the nucleotide that is underlined and bold in a marker sequence selected from the group consisting of SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, shown in Table 1.

The wildtype allele of QTL2 is linked to the nucleotide that is underlined and bold in a marker sequence selected from the group consisting of SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, and SEQ ID NO:85, shown in Table 1.

The SNPs that may be used for identification of QTL3 in a watermelon plant are present in markers M2115, M2116, and M2118. In the seeds of deposit NCIMB 42535 the resistance conferring allele of QTL3 is linked to the nucleotide that is underlined and bold in a marker sequence selected from the group consisting of SEQ ID NO:92, SEQ ID NO:94, SEQ ID NO:96, as shown in Table 1. The wildtype allele of QTL3 is linked to the nucleotide that is underlined and bold in a marker sequence selected from the group consisting of SEQ ID NO:91, SEQ ID NO:93, and SEQ ID NO:95, shown in Table 1.

In the seeds of deposit NCIMB 42539 and NCIMB 43538 the resistance conferring allele of QTL3 is linked to the nucleotide that is underlined and bold in a marker sequence selected from the group consisting of SEQ ID NO:92, SEQ ID NO:94, SEQ ID NO:96, shown in Table 1.

QTL3 located on watermelon plant chromosome 3 may comprise the resistance conferring allele of the watermelon eukaryotic translation initiation factor eIF4E gene. The sequence of the watermelon eukaryotic translation initiation factor eIF4E gene is published and can be found in the database of the NCBI. SNPs in the watermelon eIF4E gene are known to be associated with resistance to ZYMV. According to the invention in case of ZYMV resistance, the presence of QTL3 in a plant is combined with the presence of QTL1 and/or QTL2.

The flanking markers M2382 and M2386 indicate the location of QTL1, the flanking markers M2283 and M1567 indicate the location of QTL2, and flanking markers M2112 and M2122 indicate the location of QTL3. The sequences SEQ ID NO:1 and SEQ ID NO:2 are the two possible sequences of marker M2382; SEQ ID NO:41 and SEQ ID NO:42 are the two possible sequences of marker M2386; SEQ ID NO:43 and SEQ ID NO:44 are the two possible sequences of marker M2283; SEQ ID NO:87 and SEQ ID NO:88 are the two possible sequences of marker M1567; SEQ ID NO:89 and SEQ ID NO:90 are the two possible sequences of marker MM2112; SEQ ID NO:97 and SEQ ID NO:98 represent the two possible sequences of the marker M2122. Neither of the two potential marker sequences of these flanking markers are necessarily linked to the allele conferring potyvirus resistance of the specific QTL, although linkage is possible. These markers indicate the location of the QTL.

The nucleotides that are different between the marker allele linked to the potyvirus resistance conferring allele and the marker allele linked to the susceptible allele in a watermelon plant are indicated in Table 1 by using underlining and writing in bold type. A plant of the invention preferably may comprise one or more of the marker alleles that are linked to the resistance conferring allele of the QTLs.

The polymorphic nucleotides or SNPs indicated in the sequences in Table 1 may be used as molecular markers for detecting the presence of potyvirus resistance conferring alleles of QTL1 and/or QTL2 and/or QTL3 in a watermelon plant.

A plant which may comprise a potyvirus resistance allele of QTL1 may be a plant grown from a seed of which a representative sample was deposited with the NCIMB under NCIMB accession number 42537, 42539, and 42540.

A plant which may comprise a potyvirus resistance allele of QTL2 may be a plant grown from a seed of which a representative sample was deposited with the NCIMB under NCIMB accession number 42536, 42538, and 42540.

A plant which may comprise a potyvirus resistance allele of QTL3 may be a plant grown from a seed of which a representative sample was deposited with the NCIMB under NCIMB accession number 42535, 42538, and 42539.

In one embodiment the invention relates to a ZYMV resistant watermelon plant which may comprise QTL1 and/or QTL2, and optionally QTL3.

The presence of QTL1 and/or QTL2 and/or QTL3 in the genome of a watermelon plant improves its resistance to a potyvirus.

In an embodiment the invention relates to a watermelon plant that may comprise QTL1, QTL2, and optionally QTL3, and shows resistance to ZYMV.

In an embodiment the invention relates to a watermelon plant that may comprise QTL1, QTL2, and optionally QTL3, and shows resistance to ZYMV.

In an embodiment the invention relates to a watermelon plant that may comprise QTL1, QTL2, and/or QTL3, and shows resistance to WMV.

In an embodiment the invention relates to a watermelon plant (*Citrullus lanatus* subsp. *lanatus*) that may comprise a QTL1 and/or QTL2 and/or QTL3, and produces fruits that have red flesh, wherein the mature fruits of said plant preferably have flesh with soluble solids of at least 5.0, brix, preferably at least 5.5 brix, more preferably at least 6.0 brix. A "watermelon plant" as used herein is defined as a plant belonging to the species "*Citrullus lanatus* subsp. *lanatus*" that is agronomically elite, and produces fruits with red flesh. Preferably the mature fruits of this watermelon plant have flesh with soluble solids of at least 5.0 brix, preferably at least 5.5 brix, more preferably 6.0 brix and/or average sized seeds. The term 'agronomically elite watermelon plant' as used herein is defined as a watermelon plant that may comprise distinguishable agronomic traits which make the watermelon plant fit for commercial production.

"Resistance to potyvirus" as used herein is defined as a potyvirus resistance score that is on average in order of increased preference at least 1.0 lower, at least 1.5 lower, at least 2.0 lower, at least 2.5 lower, at least 3.0 lower, at least 3.5 lower, at least 4.0 lower, at least 4.5 lower, at least 5.0 lower, at least 5.5 lower, at least 6.0 lower, on a scale of 0 to 9, than the potyvirus resistance score of a watermelon plant not comprising a resistance conferring allele of QTL1 and/or QTL2, and/or QTL3.

"Resistance to ZYMV" as used herein is defined as an increase in ZYMV resistance. A ZYMV resistant watermelon plant which may comprise a resistance conferring allele of QTL1 and/or QTL2, and optionally QTL3 has a ZYMV resistance score that is on average in order of increased preference at least 1.0 lower, at least 1.5 lower, at least 2.0 lower, at least 2.5 lower, at least 3.0 lower, at least 3.5 lower, at least 4.0 lower, at least 4.5 lower, at least 5.0 lower, at least 5.5 lower, at least 6.0 lower, on a scale of 0 to 9, than the potyvirus resistance score of a watermelon plant not comprising a resistance conferring allele of QTL1 and/or QTL2, and optionally QTL3.

"Resistance to WMV" as used herein is defined as an increase in WMV resistance. A WMV resistant watermelon plant which may comprise resistance conferring allele of QTL1 and/or QTL2, and/or QTL3 has a WMV resistance score that is on average in order of increased preference at least 1.0 lower, at least 1.5 lower, at least 2.0 lower, at least 2.5 lower, at least 3.0 lower, at least 3.5 lower, at least 4.0 lower, at least 4.5 lower, at least 5.0 lower, at least 5.5 lower, at least 6.0 lower, on a scale of 0 to 9, than the WMV resistance score of a watermelon plant not comprising resistance conferring alleles of QTL1 and/or QTL2, and/or QTL3.

The "resistance score" as defined herein is assessed in the following manner. Watermelon plants in the 5/6 leaves stage are inoculated by hand with a mixture that may comprise a potyvirus. Two leaves per plant are inoculated, and after 3 to 4 days the inoculation is repeated. Plants are incubated in a climate cell and after a few days they are put in a greenhouse. After 12, 14 and 20 days following the first inoculation, the plants are phenotyped and the level of the infection is visually assessed according to the following scale: 1. no symptoms; 2. no symptoms to some chlorotic lesions on the old leaves; 3. some chlorotic lesions on the old leaves; 4. some chlorotic lesions on the old leaves to more chlorotic lesions on the old leaves; 5. more chlorotic lesions on all the leaves; 6. more chlorotic lesions to obvious mosaic and deformations on the young leaves; 7. obvious mosaic and deformations on the young leaves; 8. obvious mosaic and deformations on the young leaves to strong stunting and mosaic with deformations; 9. strong stunting and mosaic with deformations. Scores 7 and higher are considered to be susceptible.

The invention relates to seed capable of growing into a watermelon plant, wherein the watermelon plant is a plant of the invention, which may comprise QTL1 and/or QTL2, and/or QTL3, conferring resistance to a potyvirus. The invention also relates to seed harvested from a watermelon plant of the invention. The seed itself also may comprise QTL1 and/or QTL2, and/or QTL3, conferring potyvirus resistance to a watermelon plant.

The invention relates to propagation material capable of developing into a watermelon plant, and wherein the watermelon plant may comprise QTL1 and/or QTL2, and/or QTL3, conferring resistance to a potyvirus. The invention also relates to propagation material derived of a watermelon plant of the invention. The propagation material can be selected from a microspore, pollen, ovary, ovule, embryo, embryo sac, egg cell, cutting, root, hypocotyl, cotyledon, stem, leaf, flower, anther, seed, meristematic cell, protoplast, cell, or tissue culture thereof. The propagation material derived from a watermelon plant of the invention or the propagation material that is capable of growing into a watermelon plant of the invention may comprise one or more QTLs selected from the group consisting of QTL1 and/or QTL2, and/or QTL3, conferring resistance to a potyvirus.

In one embodiment, the propagation material of the invention may comprise QTL1 and/or QTL2, and/or QTL3 conferring resistance to WMV.

In another embodiment the propagation material capable of growing in to a watermelon plant of the invention may comprise QTL1 and/or QTL2, and optionally QTL3, conferring resistance to ZYMV.

The invention further provides a method for the production of a watermelon plant having potyvirus resistance by using a doubled haploid generation technique on a watermelon plant of the invention to generate a doubled haploid line which may comprise potyvirus resistance.

The invention also relates to a method of selecting a watermelon plant that may comprise QTL1 and/or QTL2, and/or QTL3, whereby the method consists of detecting a marker selected from the group consisting of SEQ ID NO:4, SEQ ID NO:6, SEQ ID NO:8, SEQ ID NO:10, SEQ ID NO:12, SEQ ID NO:14; SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:92, SEQ ID NO:94 and SEQ ID NO:96 in the genome of watermelon plants and selecting a watermelon plant that may comprise the detected marker as a watermelon plant which may comprise QTL1 and/or QTL2, and/or QTL3.

In one embodiment, the method relates to a method of selecting a watermelon plant that may comprise QTL1 whereby the method consists of detecting a marker selected from the group consisting of SEQ ID NO:4, SEQ ID NO:6, SEQ ID NO:8, SEQ ID NO:10, SEQ ID NO:12, SEQ ID NO:14; SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40 in the genome of watermelon plants and selecting a watermelon plant that may comprise the detected marker as a watermelon plant which may comprise QTL1.

In another embodiment, the method relates to a method selecting a watermelon plant that may comprise QTL2 whereby the method consists of detecting a marker selected from the group consisting of SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, in the genome of watermelon plants and selecting a watermelon plant that may comprise the detected marker as a watermelon plant which may comprise QTL2.

In another embodiment, the method relates to a method selecting a watermelon plant that may comprise QTL3 whereby the method consists of detecting a marker selected from the group consisting of SEQ ID NO:92, SEQ ID NO:94 and SEQ ID NO:96 in the genome of watermelon plants and selecting a watermelon plant that may comprise the detected marker as a watermelon plant which may comprise QTL3.

There are many different marker systems available, any marker that is genetically linked or correlated to one of the QTLs of the invention may be used. Methods to isolate, develop and utilize such markers are known in the art. In the absence of molecular markers, equivalence of QTLs may be determined by using a so-called "allelism test" or "complementation test". To perform an allelism test, material that is homozygous for a known QTL (the reference plant), is crossed with material that is also homozygous for a yet unknown QTL that causes the phenotype of potyvirus resistance (the tester plant). In case no segregation for the phenotypic trait is present in the F2 population of the cross, the QTL resulting in the phenotypic trait in the tester plant has been shown to be located on the same locus as the QTL of the invention and is thus equivalent thereto or the same.

In one preferred embodiment, the invention relates to a method of selecting a watermelon plant that may comprise QTL1 and/or QTL2, and optionally QTL3, whereby the method consists of detecting a marker selected from the group consisting of SEQ ID NO:4, SEQ ID NO:6, SEQ ID NO:8, SEQ ID NO:10, SEQ ID NO:12, SEQ ID NO:14; SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:92, SEQ ID NO:94 and SEQ ID NO:96 in the genome of watermelon plants, selecting a watermelon plant that may comprise the marker to be detected as a watermelon plant which may comprise QTL1 and/or QTL2, and optionally QTL3, and performing a phenotypical assay for ZYMV resistance, to select a watermelon plant resistant to ZYMV. The phenotypical assay for ZYMV resistance is described in Example 1 of this application.

In one preferred embodiment, the invention relates to a method of selecting a watermelon plant that may comprise QTL1 and/or QTL2, and/or QTL3, whereby the method consists of detecting a marker selected from the group consisting of SEQ ID NO:4, SEQ ID NO:6, SEQ ID NO:8, SEQ ID NO:10, SEQ ID NO:12, SEQ ID NO:14; SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:92, SEQ ID NO:94 and SEQ ID NO:96 in the genome of watermelon plants, selecting a watermelon plant that may comprise the marker to be detected as a watermelon plant which may comprise QTL1 and/or QTL2, and/or QTL3, and performing a phenotypical assay for WMV resistance, to select a watermelon plant resistant to WMV.

The phenotypical assay for WMV resistance is described in Example 2 of this application.

The invention relates to the use of QTL1 and/or QTL2, and/or QTL3, for identifying and/or developing a watermelon plant showing resistance to a potyvirus.

In a preferred embodiment the invention relates to the use of QTL1 and/or QTL2, and/or QTL3, for identifying and/or developing a watermelon plant showing resistance to WMV. The invention relates to a marker selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, or a marker derived therefrom, wherein the marker is linked to QTL1.

In another aspect, the invention also relates to a marker selected from the group consisting of SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86 or a marker derived therefrom, wherein the marker is linked to QTL2.

The invention also relates to a marker selected from the group consisting of SEQ ID NO:92, SEQ ID NO:94, SEQ ID NO:96 or a marker derived therefrom, wherein the marker is linked to QTL3.

In one embodiment, the invention relates to a set of markers, which may comprise two or more markers selected from the group consisting of SEQ ID NO:4, SEQ ID NO:6, SEQ ID NO:8, SEQ ID NO:10, SEQ ID NO:12, SEQ ID NO:14; SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:92, SEQ ID NO:94, SEQ ID NO:96, wherein the marker is linked to one or more of QTL1, QTL2, QTL3.

In another embodiment the invention relates to the use of a marker or marker set selected from the group consisting of SEQ ID NO:4, SEQ ID NO:6, SEQ ID NO:8, SEQ ID NO:10, SEQ ID NO:12, SEQ ID NO:14; SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:92, SEQ ID NO:94, SEQ ID NO:96, for identifying a watermelon plant which may comprise one or more of QTL1 and/or QTL2, and/or QTL3.

The invention also relates to the use of said markers to develop other markers linked to one or more of the QTLs of the invention.

The invention relates to a method for producing a watermelon plant which shows resistance to a potyvirus, said method which may comprise:

a) crossing a (parent) plant that may comprise QTL1 and/or QTL2, and/or QTL3 with another (parent) plant to obtain an F1 population;

b) optionally performing one or more rounds of selfing and/or crossing a plant from the F1 to obtain a further generation population; and c) selecting from the population a plant that may comprise QTL1 and/or QTL2, and/or QTL3 and shows resistance to a potyvirus.

The QTLs of the invention may be introduced into any other watermelon plant by introgression from a plant grown from a seed of which a representative sample was deposited with the NCIMB under deposit number NCIMB 42535, NCIMB 42536, NCIMB 42537, NCIMB 42538, NCIMB 42539, NCIMB 42540 or any plant derived from these deposits and which may comprise the QTLs of the invention. Watermelon plants that have one or more of the resistance conferring alleles of the QTLs as found in plants grown from seeds deposited under deposit number NCIMB 42535, NCIMB 42536, NCIMB 42537, NCIMB 42538, NCIMB 42539, NCIMB 42540 but are not directly obtained therefrom also fall under the invention, except plants that have only QTL3 and are resistant to ZYMV. As used herein, "introgression" in a genetic context, refers to a process wherein a genetic region or locus is introduced from one genetic background into a new genetic background, either within or outside the same species. Introgression can thus be achieved by various plant breeding methods such as crossing and/or backcrossing and selecting. Introgression can encompass a breeding process that takes multiple generations, for example when the trait is recessive and/or involves more than one gene. Introgression is used herein to also describe the whole process.

The parent plant that provides the trait of the invention is not necessarily a watermelon plant grown directly from the deposited seeds. The parent can also be a progeny watermelon plant from the seed or a progeny watermelon plant from seeds that are identified to have the genetic trait of the invention by other means.

The invention additionally provides a method of introducing another desired trait into a watermelon plant which shows potyvirus resistance, which may comprise:

a) crossing a (parent) watermelon plant that may comprise QTL1 and/or QTL2, and/or QTL3 and shows resistance to a potyvirus, with a second watermelon plant that may comprise a desired trait to produce F1 progeny;

b) selecting an F1 progeny that may comprise QTL1 and/or QTL2, and/or QTL3 leading to the trait of potyvirus resistance and the desired trait;

c) crossing the selected F1 progeny with either parent, to produce backcross progeny;

d) selecting backcross progeny which may comprise the desired trait and the trait of potyvirus resistance, and e) optionally repeating steps c) and d) one or more times in succession to produce selected fourth or higher backcross progeny that may comprise the desired trait and the trait of potyvirus resistance. The invention includes a watermelon plant produced by this method.

The invention also relates to a method for the production of a watermelon plant having the trait of potyvirus resistance by using a seed that may comprise QTL1 and/or QTL2, and/or QTL3, in its genome for growing the said watermelon plant. The seed is suitably a seed of which a representative sample was deposited with the NCIMB under deposit number NCIMB 42535, NCIMB 42536, NCIMB 42537, NCIMB 42538, NCIMB 42539, NCIMB 42540. The invention also relates to a method for seed production which may comprise growing a watermelon plant from seed of which a representative sample was deposited with the NCIMB under number NCIMB 42535, NCIMB 42536, NCIMB 42537, NCIMB 42538, NCIMB 42539, NCIMB 42540, allowing the watermelon plant to produce seed, and harvesting this seed. Production of the seeds is suitable done by crossing or selfing. In one embodiment, the invention relates to a method for the production of a watermelon plant having potyvirus resistance by using tissue culture. The invention furthermore relates to a method for the production of a watermelon plant having potyvirus resistance by using vegetative reproduction.

In one embodiment, the invention relates to a method for the production of a watermelon plant having the trait of potyvirus resistance by using a method for genetic modification to introduce the said trait into the watermelon plant. Genetic modification may comprise transgenic modification or transgenesis, using a gene from a non-crossable species or a synthetic gene, and cisgenic modification or cisgenesis, using a natural gene, coding for an (agricultural) trait, from the crop watermelon plant itself or from a sexually compatible donor plant.

The invention relates to the use of a watermelon plant as claimed herein in a breeding program to develop watermelon plants having resistance to potyvirus resistance, ZYMV resistance and/or WMV resistance. The invention also relates to a breeding method for the development of watermelon plants having potyvirus resistance, ZYMV resistance and/or WMV resistance wherein germplasm which may comprise one or more of the QTLs of the invention are used. In a further embodiment the invention relates to a method for the production of a watermelon plant having the trait of potyvirus resistance wherein progeny or propagation material of a plant which may comprise QTL1 and/or QTL2, and/or QTL3 conferring said trait is used as a source to introgress the said trait into another watermelon plant.

The invention provides a watermelon plant having potyvirus resistance, which plant is obtainable by any of the methods herein described and/or familiar to the skilled person.

The invention further involves a method of determining the genotype of a plant of the invention, having the trait of potyvirus resistance and which may comprise one or more QTLs of the invention, which may comprise obtaining a sample of nucleic acids from said plant and a reference plant not comprising the QTLs of the invention and detecting in the nucleic acids of said samples a plurality of polymorphisms. This method may additionally comprise the step of storing the results of detecting the plurality of polymorphisms on a computer readable medium. The plurality of polymorphisms are indicative of one or more of the potyvirus resistance alleles.

There are various ways of obtaining genotype data from a nucleic acid sample. Genotype data may be gathered which is specific for certain phenotypic traits (e.g. gene sequences), but also patterns of random genetic variation may be obtained to construct a so-called DNA fingerprint. Depending on the technique used, a fingerprint may be obtained that is unique for a watermelon plant carrying the resistance allele(s) of the invention. Obtaining a unique DNA fingerprint depends on the genetic variation present in a variety and the sensitivity of the fingerprinting technique. A technique known in the art to provide a good fingerprint profile is called AFLP fingerprinting technique (See generally U.S. Pat. No. 5,874,215), but there are many other marker based techniques, such as RFLP (or Restriction fragment length polymorphism), SSLP (or Simple sequence length polymorphism), RAPD (or Random amplification of polymorphic DNA) VNTR (or Variable number tandem repeat), Microsatellite polymorphism, SSR (or Simple sequence repeat), STR (or Short tandem repeat), SFP (or Single feature polymorphism) DarT (or Diversity Arrays Technology), RAD markers (or Restriction site associated DNA markers) (e.g. Baird et al. PloS One Vol. 3 e3376, 2008; Semagn et al. African Journal of Biotechnology Vol. 5 number 25 pp. 2540-2568, 29 Dec., 2006). Nowadays, sequence-based methods are utilizing Single Nucleotide Polymorphisms (SNPs) that are randomly distributed across genomes, as a common tool for genotyping (e.g. Elshire et al. PloS One Vol. 6: e19379, 2011; Poland et al. PloS One Vol. 7: e32253; Truong et al. PloS One Vol. 7 number 5: e37565, 2012).

With any of the aforementioned genotyping techniques, polymorphisms may be detected when the genotype and/or sequence of the plant of interest is compared to the genotype and/or sequence of one or more reference plants. As used herein, the genotype and/or sequence of a reference plant may be derived from, but is not limited to, any one of the following: parental lines, closely related plant varieties or species, complete genome sequence of a related plant variety or species, or the de novo assembled genome sequence of one or more related plant varieties or species.

For example, it is possible to detect polymorphisms for the presence or absence of the potyvirus resistance conferring allele(s) by comparing the genotype and/or the sequence of a watermelon plant carrying the potyvirus resistance conferring allele(s), representative seed of which has been deposited under NCIMB 42535, NCIMB 42536, NCIMB 42537, NCIMB 42538, NCIMB 42539, NCIMB 42540, with the genotype and/or the sequence of one or more reference plants. The reference plant(s) used for comparison in this example may for example be, but is not limited to, any of the watermelon varieties not comprising potyvirus resistance and/or parent lines, ancestor, or progeny plants thereof as.

The polymorphism revealed by these techniques may be used to establish links between genotype and phenotype. The polymorphisms may thus be used to predict or identify certain phenotypic characteristics, e.g. the resistance provided by the potyviruses resistance conferring allele(s), individuals, or even species. The polymorphisms are generally called markers. It is common practice for the skilled artisan to apply molecular DNA techniques for generating polymorphisms and creating markers.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer readable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

In one embodiment the plant which may comprise the QTL is a plant of an inbred line, a hybrid, a doubled haploid, or of a segregating population.

In one embodiment the plant of the invention, i.e. a plant which may comprise the QTL of the invention, is an agronomically elite watermelon plant.

In the context of this invention an agronomically elite watermelon plant is a plant having a genotype that as a result of directed crossing and selection by human intervention results into an accumulation of distinguishable and desirable agronomic traits which allow a producer to harvest a product of commercial significance.

In the course of breeding a new watermelon plant carrying the QTL of the invention, desirable agronomic traits may be introduced into said watermelon plant independently of the QTL of the invention. As used herein, "desirable traits" include but are not limited to e.g. improved yield, fruit shape, fruit size, fruit colour, seed size, plant vigor, plant height, and resistance to one or more diseases or disease causing organisms. Any one of these desirable traits may be combined with the QTL of the invention.

In yet a further embodiment the agronomically elite watermelon plant of the invention is an inbred line or a hybrid.

As used herein, a plant of an inbred line is a plant of a population of plants that is the result of three or more rounds of selfing, or backcrossing; or which plant is a double haploid. An inbred line may e.g. be a parent line used for the production of a commercial hybrid.

As used herein, a hybrid plant is a plant which is the result of a cross between two different plants having different genotypes. More in particular, a hybrid plant is the result of a cross between plants of two different inbred lines, such a hybrid plant may e.g. be a plant of a commercial F1 hybrid variety.

In one embodiment the plant which may comprise the QTL of the invention is an F1 hybrid variety.

TABLE 1

Marker information

| Marker name | SEQ ID | Sequence |
|---|---|---|
| M2382 (wildtype) | SEQ ID NO: 1 | CAAATAGATATGGGACTTGAATATCTAGATACATGGAT TTTAATTTTAAAAATAAAATAAAAAAGAGAAGTTATTA TAAATAGAAAAAATATCAAACTAACTACAAATATAAA AAAACTTTTACTGTCTATTAGCGATAGAACGCGATAGA CTTCTATCACATGAGCGATATTGAGCAATGGACTTCTG TCAGTCTATCGC |

TABLE 1-continued

Marker information

| Marker name | SEQ ID | Sequence |
|---|---|---|
| M2382 (mutant) | SEQ ID NO: 2 | CAAATAGATATGGGACTTGAATATCTAGATACATGGAT TTTAATTTTAAAAATAAAATAAAAAAGAGAAGTTATTA TAAATAGAAAAAATATCAAACTAATTACAAATATAAA AAAACTTTTACTGTCTATTAGCGATAGAACGCGATAGA CTTCTATCACATGAGCGATATTGAGCAATGGACTTCTG TCAGTCTATCGC |
| M4996 (wildtype) | SEQ ID NO: 3 | TGTAAAGAAGATATGTAAAGGTACACGAAGAGCTTCA GCAACATGTGTATGTCCTGCAACCCAAATCAAACAAGC ACAGTGTGAAATTTGAAAACTAACCCTTCAATAGAAGT TCTATTCCAsCCATTCAATTAAwAATTTAGTAAACAATT ATrTGAATCAAATGTTTAATGATAGACTTTATTGTGGGA AATTGCCTGC |
| M4996 (mutant) | SEQ ID NO: 4 | TGTAAAGAAGATATGTAAAGGTACACGAAGAGCTTCA GCAACATGTGTATGTCCTGCAACCCAAATCAAACAAGC ACAGTGTGAAATTTGAAAACTAACCGTTCAATAGAAGT TCTATTCCAsCCATTCAATTAAwAATTTAGTAAACAATT ATrTGAATCAAATGTTTAATGATAGACTTTATTGTGGGA AATTGCCTGC |
| M4997 (wildtype) | SEQ ID NO: 5 | TTTGAAGTGACAATATTTATCATTTGTGGATTTAATCTC yACGATTATATTGTTAGTTCCAATATATATATAACCCTT GCATGTTGGAGAwTGGTGAGGCGrAGGCTTTTCTTAGG GAGACTGGTACCCCAACAAACTCTTCTTTTCCCCTTGCC CCCATTATCTCTTGTTGGTCCmCATTTGTTGCCGCTAAC rGAAAGT |
| M4997 (mutant) | SEQ ID NO: 6 | TTTGAAGTGACAATATTTATCATTTGTGGATTTAATCTC yACGATTATATTGTTAGTTCCAATATATATATAACCCTT GCATGTTGGAGAwTGGTGAGGCArAGGCTTTTCTTAGG GAGACTGGTACCCCAACAAACTCTTCTTTTCCCCTTGCC CCCATTATCTCTTGTTGGTCCmCATTTGTTGCCGCTAAC rGAAAGT |
| M4998 (wildtype) | SEQ ID NO: 7 | AGATTGAGTTATAATTTTCTGGTGGTTAATCATACAGT GTAAGCTTCAATTGAGTCGTGAACTTCATTTTACTACTA ATGAGCTATATGTATCGTCTTTGATTCTGGATwAGCAT GAAAGCTTTCTTCATGTTAAATCACAAACTAAATGGTT TTTkATTATGATCAGGTGGCAAAAAACTATTAACACCT CAGCCTCGGT |
| M4998 (mutant) | SEQ ID NO: 8 | AGATTGAGTTATAATTTTCTGGTGGTTAATCATACAGT GTAAGCTTCAATTGAGTCGTGAACTTCATTTTACTACTA ATGAGCTATATGTATCGTCTTTGGTTCTGGATwAGCAT GAAAGCTTTCTTCATGTTAAATCACAAACTAAATGGTT TTTkATTATGATCAGGTGGCAAAAAACTATTAACACCT CAGCCTCGGT |
| M4999 (wildtype) | SEQ ID NO: 9 | AGGTCCTCACCAATATCCAGATCATCTTCAACCTTTGA ACGTGGATCCCCGCCCGAATCATCTTGTTCAGCTGCAC CCGTCCCACGTAAAGGAGGAGGGGCCAGAGGCGGCAG TACCTCyTCTTGTACAAAGGCCCGAAAGTTGTTCTTTGA GGGmTTTrCTTTTGAGCAAAATACTTCCAGrAAATTATT CAGACAACCT |
| M4999 (mutant) | SEQ ID NO: 10 | AGGTCCTCACCAATATCCAGATCATCTTCAACCTTTGA ACGTGGATCCCCGCCCGAATCATCTTGTTCAGCTGCAC CCGTCCCACGTAAAGGAGGAGGGGGCAGAGGCGGCAG TACCTCyTCTTGTACAAAGGCCCGAAAGTTGTTCTTTGA GGGmTTTrCTTTTGAGCAAAATACTTCCAGrAAATTATT CAGACAACCT |
| M5000 (wildtype) | SEQ ID NO: 11 | TATCCATTACTTCAGCGAACCGCCATTTCATTGTTTTTA TCCCATGGCTTTGTCTTCGTTTCyCATTTCTTCCTCTGTA ACGATTCGATTAGCACCCrAATACAATTCGATTGCGATT TCGTTCATCGAGyCCCAAACATGAGGTATACCTATCGC TTCTTGATTCTTTTCGTTTCTTGTTCTATACAAAACGAT GAGGAA |

TABLE 1-continued

Marker information

| Marker name | SEQ ID | Sequence |
|---|---|---|
| M5000 (mutant) | SEQ ID NO: 12 | TATCCATTACTTCAGCGAACCGCCATTTCATTGTTTTTA<br>TCCCATGGCTTTGTCTTCGTTTCyCATTTCTTCCTCTGTA<br>ACGATTCGATTAGCACCCrAACACAATTCGATTGCGATT<br>TCGTTCATCGAGyCCCAAACATGAGGTATACCTATCGC<br>TTCTTGATTCTTTTCGTTTCTTGTTCTATACAAAACGAT<br>GAGGAA |
| M5001 (wildtype) | SEQ ID NO: 13 | ATTTTTTGTCTrTTTCTTTTTCTGTGTTyTGTTTCGTGCTT<br>TAGGCTAAAyTTATTTGTTTTTTACTTGCAGTGATAGAT<br>GGCTGACCTAAAAATTAAGGCTGAGAATCGTTTTTACA<br>GTTAAGCTwCrAGCCTCTCATCTCACATCGGATTGCAAA<br>TAGrATAATCAAAGAGAAGCTTrCAGAGAGACAACTTC<br>AATTGT |
| M5001 (mutant) | SEQ ID NO: 14 | ATTTTTTGTCTrTTTCTTTTTCTGTGTTyTGTTTCGTGCTT<br>TAGGCTAAAyTTATTTGTTTTTTACTTGCAGTGATAGAT<br>GGCTGACCTAAAAATTAAGGTTGAGAATCGTTTTTACA<br>GTTAAGCTwCrAGCCTCTCATCTCACATCGGATTGCAAA<br>TAGrATAATCAAAGAGAAGCTTrCAGAGAGACAACTTC<br>AATTGT |
| M5003 (wildtype) | SEQ ID NO: 15 | TGATTTAATTTAkATTATCAATTTATGCATArTTACTAAA<br>kTAAGCTAACATGTATTTyCTCTTTTGAAGTTGGAGGTT<br>CAATTCTCCCTCTCCTAAyTATTGTACTAAAAAAAATw<br>ATACCATCATCTTAmAATArAGAAAAATTGTAATTGAA<br>TAGTTATAAATAAAATAAAAGGTTAAAATATCCTTTCA<br>CAAAGTT |
| M5003 (mutant) | SEQ ID NO: 16 | TGATTTAATTTAkATTATCAATTTATGCATArTTACTAAA<br>kTAAGCTAACATGTATTTyCTCTTTTGAAGTTGGAGGTT<br>CAATTCTCCCTCTCCTAAyTAGTGTACTAAAAAAAAAT<br>wATACCATCATCTTAmAATArAGAAAAATTGTAATTGA<br>ATAGTTATAAATAAAATAAAAGGTTAAAATATCCTTTC<br>ACAAAGTT |
| M2384 (wildtype) | SEQ ID NO: 17 | ACAAGCTCTTCATGTAACCAATTTCTGGTGGTATTGTGC<br>CAGAGAGACTGTTGCAACTCAAATCAAGTAGAGTTAGT<br>TTCTCCAGGTTCTTAATAGACTTCGGGATTGACCCTGTC<br>AGTAGATTATTATTGAGTATAAGTTTATTCAAATAACT<br>GAAATTTCCAAAGCTCTGAGGAATTTCACCAGTGAAGC<br>TGTTTCGAC |
| M2384 (mutant) | SEQ ID NO: 18 | ACAAGCTCTTCATGTAACCAATTTCTGGTGGTATTGTGC<br>CAGAGAGACTGTTGCAACTCAAATCAAGTAGAGTTAGT<br>TTCTCCAGGTTCTTAATAGACTTTGGGATTGACCCTGTC<br>AGTAGATTATTATTGAGTATAAGTTTATTCAAATAACT<br>GAAATTTCCAAAGCTCTGAGGAATTTCACCAGTGAAGC<br>TGTTTCGAC |
| M5004 (wildtype) | SEQ ID NO: 19 | GrAAGAAATTTATTTTTTTAAAAAAAAATGATTCTAT<br>CCATTTTCCAGTCAACTTTACGGAAAwTTGTACATAAT<br>CATTTCTTTTCCTTCyTTTTTTTTTTTTyTTTCAAGAAGAC<br>AACTATTTCCCTyCAAGTTwTGAGGTTATTTTTTATAAA<br>GTTGACTGGAGAATACTATTTTCCTAAGAATTCCAATC<br>AATCTA |
| M5004 (mutant) | SEQ ID NO: 20 | GrAAGAAATTTATTTTTTTAAAAAAAAATGATTCTAT<br>CCATTTTCCAGTCAACTTTACGGAAAwTTGTACATAAT<br>CATTTCTTTTCCTTCyTTTTTTTCTTTTyTTTCAAGAAGA<br>CAACTATTTCCCTyCAAGTTwTGAGGTTATTTTTTATAA<br>AGTTGACTGGAGAATACTATTTTCCTAAGAATTCCAAT<br>CAATCTA |
| M5005 (wildtype) | SEQ ID NO: 21 | AAAAGAAGAAGAAGAAAAAAAAACTACTTTCTTTTAA<br>TTGATAATAAAATAAAAAGAAATTTAAGAGTGAArAAG<br>ATATTTATAGTCTTAATTTAAAAAAGAAwwAAAArwAA<br>AAAAwAAAATGGTTACTTTAACGGACCAACATTyyCTAA<br>CATATACAATAATTAAAAArATATATGTATAGTAArGTT<br>AAAAAAwGTCT |

TABLE 1-continued

Marker information

| Marker name | SEQ ID | Sequence |
|---|---|---|
| M5005 (mutant) | SEQ ID NO: 22 | AAAAGAAGAAGAAGAAAAAAAAACTACTTTCTTTTAA TTGATAATAAAATAAAAAGAAATTTAAGAGTGArAAG ATATTTATAGTCTTAATTTAAAAAAAAAwwAAAArwAA AAAAwAAAATGGTTACTTTAACGGACCAACATyyCTAA CATATACAATAATTAAAAArATATATGTATAGTAArGTT AAAAAAwGTCT |
| M5007 (wildtype) | SEQ ID NO: 23 | GGAAATATTAGAGGGAGGAArAAATAAAGArrAAAAGA TTGArTACTATykAATTTGAGTTATTTAACACCGACTTAT GAAGTTGGTAAsCTAATACCyTTTAAAATTTTAAAATrTT TCATTTTAAAAGTATAAATAATAGATTTAGAAGATACT TTTGAATGTTAACATsACATTTTAAAwTTTAAATAATAA TyGAAG |
| M5007 (mutant) | SEQ ID NO: 24 | GGAAATATTAGAGGGAGGAArAAATAAAGArrAAAAGA TTGArTACTATykAATTTGAGTTATTTAACACCGACTTAT GAAGTTGGTAAsCTAATACCyTCTAAAATTTTAAAATrT TTCATTTTAAAAGTATAAATAATAGATTTAGAAGATAC TTTTGAATGTTAACATsACATTTTAAAwTTTAAATAATA ATyGAAG |
| M5008 (wildtype) | SEQ ID NO: 25 | GAAAAAGATTGTGATAATAGTrAACAGTAAAATTAGTC AkGTATkTGGACATAGGyGGTAGACTTCAATTTGTGTTT TTAAACGAArTTTTAATTATACTTTTGTAGGTTTAAAGT TCTTTTTTAATTATCATTATTACTCTrAAATTACCArAAA AACGACATTTTGCTCmTTTCTACTAAAATAAAGArAATA TmATTG |
| M5008 (mutant) | SEQ ID NO: 26 | GAAAAAGATTGTGATAATAGTrAACAGTAAAATTAGTC AkGTATkTGGACATAGGyGGTAGACTTCAATTTGTGTTT TTAAACGAArTTTTAATTATACTCTTGTAGGTTTAAAGT TCTTTTTTAATTATCATTATTACTCTrAAATTACCArAAA AACGACATTTTGCTCmTTTCTACTAAAATAAAGArAATA TmATTG |
| M5010 (wildtype) | SEQ ID NO: 27 | AAAGACTATAAAAkAGCACTTATATATATTTTCCATTTT TCTTrAAkGATGmTrAAAAGATGTTAATCTAGTTGAGrTG TTCrTCCrCACTACTCTTATyCCAyCATCCTTAGTATTTTG TTAAAAAAAAAArAAAAAAAkAwTCTTCATTTTTAACTCT TTTGATGATsTAGTAATTGGTATTGTAAAATGTTCTTGA AAT |
| M5010 (mutant) | SEQ ID NO: 28 | AAAGACTATAAAAkAGCACTTATATATATTTTCCATTTT TCTTrAAkGATGmTrAAAAGATGTTAATCTAGTTGAGrTG TTCrTCCrCACTACTCTTATyTCAyCATCCTTAGTATTTTG TTAAAAAAAAAArAAAAAAAkAwTCTTCATTTTTAACTCT TTTGATGATsTAGTAATTGGTATTGTAAAATGTTCTTGA AAT |
| M5011 (wildtype) | SEQ ID NO: 29 | TTTTAACTCTTTTCCCCTGTGTATGTATGTACTTGCAGT TTAATAGATGAACGTAGCTTAGAAGTGATAGCATTTGC ATCTTTACTCTTACGGCCATTTCAwTTTCTGAAACTGAA AGATTAAAACAAAGATGGCyATCAATTTCTAATTTACC TTGCCTTCAAAGATTTGGwACTGCTTAATTCTTTCTTGA AATTCTCT |
| M5011 (mutant) | SEQ ID NO: 30 | TTTTAACTCTTTTCCCCTGTGTATGTATGTACTTGCAGT TTAATAGATGAACGTAGCTTAGAAGTGATAGCATTTGC ATCTTTACTCTTACGGCCATTTCCCwTTTCTGAAACTGAA AGATTAAAACAAAGATGGCyATCAATTTCTAATTTACC TTGCCTTCAAAGATTTGGwACTGCTTAATTCTTTCTTGA AATTCTCT |
| M5012 (wildtype) | SEQ ID NO: 31 | AAACTTATAyGATTTTACAATTTCTATAACTATTGTAA GTTTAAGAATCCAATTTTAATACTTGCAyAAATTTGAGr ACTCAATTTTTAyAATTGAAACAATTGAGAGTTCrAAGA TATAATTGCAAyTmCTATkGTACTTTAAGGTGrTTTTTrC AArTTTTCyTTAAAGrTAAATrAAkATTTTATCTACTTyAT TGC |

TABLE 1-continued

Marker information

| Marker name | SEQ ID | Sequence |
| --- | --- | --- |
| M5012 (mutant) | SEQ ID NO: 32 | AAACTTATAyGATTTTTACAATTTCTATAACTATTGTAAGTTTAAGAATCCAATTTTAATACTTGCAyAAATTTGAGrACTCAATTTTTAyAATTGAAACTATTGAGAGTTCrAAGATATAATTGCAAyTmCTATkGTACTTTAAGGTGrTTTTTrCAArTTTTCyTTAAAGrTAAATrAAkATTTTATCTACTTyATTGC |
| M5014 (wildtype) | SEQ ID NO: 33 | CTCGAATTGATTAGATGATATTTCGTGTTrATGCGTCyATTGTGCACGACATCrACGAGATTAATCTCTACGTGTCCCAATGATTCCTGTGrAAAAGATCATTTTGAACAATTTCGAACCGATTCGTAAGCAAGAGGGGAAmAAATTTGTGATGTGATGTGATGTGATGTTACCTTTGAGAGGAAACTGAAAAGGCTGCTC |
| M5014 (mutant) | SEQ ID NO: 34 | CTCGAATTGATTAGATGATATTTCGTGTTrATGCGTCyATTGTGCACGACATCrACGAGATTAATCTCTACGTGTCCCAATGATTCCTGTGrAAAAGATCGTTTTGAACAATTTCGAACCGATTCGTAAGCAAGAGGGGAAmAAATTTGTGATGTGATGTGATGTGATGTTACCTTTGAGAGGAAACTGAAAAGGCTGCTC |
| M5015 (wildtype) | SEQ ID NO: 35 | GATGTTTCGCCAGGAGAAGAATTmGATAAGGTTTTTCAGCTATTTCTkATGGAAAATTGATAGAtsCAATGCTTGAATGTTTGAArGATTGGAATGGTGTTCCsCTTCCTCTTAGTTAGATTGTGTTGTTTTmTGTTGTGTCCATACAAGGAyACAAGTTACkTTTCTAAACCCATATATTyTTTTAATGTATACATTTC |
| M5015 (mutant) | SEQ ID NO: 36 | GATGTTTCGCCAGGAGAAGAATTmGATAAGGTTTTTCAGCTATTTCTkATGGAAAATTGATAGAtsCAATGCTTGAATGTTTGAArGATTGGAATGGTGCTCCsCTTCCTCTTAGTTAGATTGTGTTGTTTTmTGTTGTGTCCATACAAGGAyACAAGTTACkTTTCTAAACCCATATATTyTTTTAATGTATACATTTC |
| M5016 (wildtype) | SEQ ID NO: 37 | TTTTACTAGTTTGGAArGATGTTTTTyCrrATTCTATTAACCTyTCwTTCTTGCCGATrAAATTTGGGAATAATGAATTTTGGTCGTTTGTTATTATTTTTTTTTTTACAATATATGGGrTGGGGAGTTGAACCTTTGACTTAAGATTGATAATACAAACATrATGTCAGTTAAGGTATGCTCGTTTTGGTTTGATCGTTG |
| M5016 (mutant) | SEQ ID NO: 38 | TTTTACTAGTTTGGAArGATGTTTTTyCrrATTCTATTAACCTyTCwTTCTTGCCGATrAAATTTGGGAATAATGAATTTTGGTCGTTTGTTATTATTTTCTTTTTTACAATATATGGGrTGGGGAGTTGAACCTTTGACTTAAGATTGATAATACAAACATrATGTCAGTTAAGGTATGCTCGTTTTGGTTTGATCGTTG |
| M5017 (wildtype) | SEQ ID NO: 39 | GCrwAGCTTAATTGGTAAGGACACAAGATATTCACrTTTCTATATATTGGTTAGATAkTTTTCAyTTTTGGGTGATATAAGCCCTACTCAArAGGATCTCCTAyCAATTGAAGTAGCTAATTGTATmTTAACTTATATAGATAGCTATGATCTTCCATTTGTTTTAGyTCGCTTCAGACTTTGGTCGCACTCTCAAkATTA |
| M5017 (mutant) | SEQ ID NO: 40 | GCrwAGCTTAATTGGTAAGGACACAAGATATTCACrTTTCTATATATTGGTTAGATAkTTTTCAyTTTTGGGTGATATAAGCCCTACTCAArAGGATCTCATAyCAATTGAAGTAGCTAATTGTATmTTAACTTATATAGATAGCTATGATCTTCCATTTGTTTTAGyTCGCTTCAGACTTTGGTCGCACTCTCAAkATTA |
| M2386 (wildtype) | SEQ ID NO: 41 | TTAGTGGTCGAATAACTGTGAGAACCAAAACAGTTATTTTCTATAAAGTTTACAGACTAAAAGAGAAACTTGAAAGTTCATCCACCAAAATAGATTAAAGGTAAAATTGTAGACGCCAAAAAATACAGTTTTTTTAATGTTCAAGAATCAAAATCGAATGATCTTAGAAGTTTGTGGACTAAAAAGATGAGTTTTCTCA |

TABLE 1-continued

Marker information

| Marker name | SEQ ID | Sequence |
|---|---|---|
| M2386 (mutant) | SEQ ID NO: 42 | TTAGTGGTCGAATAACTGTGAGAACCAAAACAGTTATT TTCTATAAAGTTTACAGACTAAAAGAGAAACTTGAAAG TTCATCCACCAAAATAGATTAAAGCTTAAAATTGTAGA CGCCAAAAAATACAGTTTTTTTTAATGTTCAAGAATCA AAATCGAATGATCTTAGAAGTTTGTGGACTAAAAAGAT GAGTTTTCTCA |
| M2283 (wildtype) | SEQ ID NO: 43 | TGATCATCTGCAGCTCACCAAAGTCCTCATGGGATTCC ATCTAGAATATGAATCAATCGTGTTGCCTTATTACACC GCAATCCTTTGTCATGTCTAGATGTAGCAATCCAAGAA ATTTTGTTTGAGGAGAAAAGACTTGGCATAGTCTCCTT CCTATCATCTGATGTTGCTCTCATGACCATTCATTCACG ACCTGCAAAT |
| M2283 (mutant) | SEQ ID NO: 44 | TGATCATCTGCAGCTCACCAAAGTCCTCATGGGATTCC ATCTAGAATATGAATCAATCGTGTTGCCTTATTACACC GCAATCCTTTGTCATGTCTAGATGCAGCAATCCAAGAA ATTTTGTTTGAGGAGAAAAGACTTGGCATAGTCTCCTT CCTATCATCTGATGTTGCTCTCATGACCATTCATTCACG ACCTGCAAAT |
| M2285 (wildtype) | SEQ ID NO: 45 | ACTTCCCGTTTAAGGCACCAAATATAATGGTGAATATA ATTATTTATAACCTTACTATTTCAAAATCCTATTTACTA CGGTATTTATTATTTTTCACTTACCTATCTCTTTTTTTCT TTGCGATAGAGTTACTATTTCCTACCTAAACAAAAGTA GTTTACACTCCAAACATATACTATTATAATCAGATTAA AATAGTTT |
| M2285 (mutant) | SEQ ID NO: 46 | ACTTCCCGTTTAAGGCACCAAATATAATGGTGAATATA ATTATTTATAACCTTACTATTTCAAAATCCTATTTACTA CGGTATTTATTATTTTTCACTTATCTATCTCTTTTTTTCT TTGCGATAGAGTTACTATTTCCTACCTAAACAAAAGTA GTTTACACTCCAAACATATACTATTATAATCAGATTAA AATAGTTT |
| M4938 (wildtype) | SEQ ID NO: 47 | TAATAGTAATGTCrAAyTGArTAGGGTAATATTGTGCAG CTTAAATGAGAAATGATTTyCCTATTTATAAATTrGTGT CATGGTCATGTATACCTTAAGTCGrCCTAAATCATGAAG GAAATATCTCrTGGTCACmTArGAAAGCCTACTTTAGTT ATTAAATCTTCTAyATAGTTGAGAGTTGTAAATGATGTT ATTCAC |
| M4938 (mutant) | SEQ ID NO: 48 | TAATAGTAATGTCrAAyTGArTAGGGTAATATTGTGCAG CTTAAATGAGAAATGATTTyCCTATTTATAAATTrGTGT CATGGTCATGTATACCTTAAGTTGrCCTAAATCATGAAG GAAATATCTCrTGGTCACmTArGAAAGCCTACTTTAGTT ATTAAATCTTCTAyATAGTTGAGAGTTGTAAATGATGTT ATTCAC |
| M4939 (wildtype) | SEQ ID NO: 49 | TCCAAAACTATTATCTTCTTTGGTCAAATATCTGATAAA TGACATTAAATACAGAAGGCAAGAAAACAACTCGAGA AGCAATTCTACAATTAACTGTAACAATATTGATACATG GACTAATTTCTCCTATGCCTAACTGAACCTTTyCCATCT CAAGAATAACTTACCAATAAmTATGAGATCGrATACTC TGAACTCAGG |
| M4939 (mutant) | SEQ ID NO: 50 | TCCAAAACTATTATCTTCTTTGGTCAAATATCTGATAAA TGACATTAAATACAGAAGGCAAGAAAACAACTCGAGA AGCAATTCTACAATTAACTGTAACTATATTGATACATG GACTAATTTCTCCTATGCCTAACTGAACCTTTyCCATCT CAAGAATAACTTACCAATAAmTATGAGATCGrATACTC TGAACTCAGG |
| M4940 (wildtype) | SEQ ID NO: 51 | ACCAsGAGCCATTTAATTTCyCTmTCCTTACATTTAATA TAATTGGrTCyGTrTCTAATATTGGGTTGArGTTTTAAGT AATCTATGAGCCATGAGGTTCAAAAAAATATGCTATCTC GAGCTATCTCACTTTATTTATTyGTGGAAAGAATTCTCG TGGTTATGGTAATGTTATTTTGGGTAGATTGGACAmTT ATATTTT |

TABLE 1-continued

Marker information

| Marker name | SEQ ID | Sequence |
|---|---|---|
| M4940 (mutant) | SEQ ID NO: 52 | ACCAsGAGCCATTTAATTTCyCTmTCCTTACATTTAATA TAATTGGrTCyGTrTCTAATATTGGGTTGArGTTTTAAGT AATCTATGAGCCATGAGGTTCGAAAAATATGCTATCTC GAGCTATCTCACTTTATTTATTyGTGGAAAGAATTCTCG TGGTTATGGTAATGTTATTTTGGGTAGATTGGACAmTT ATATTTT |
| M4941 (wildtype) | SEQ ID NO: 53 | GATCCTTTGAATAGATTTCTATTTCCTCGGTGAGGGAA GATCTATCTGGTCTTAGAGTTGAAAAGTTACTAGACGA AAGTGGCGATGCAGTTGGAGTACGTGGAGAAGGAGCT AGAGAATTTGCAGCAGAAATATCTGTGGAAAGTTGGG GGAGAGGAGGAGGTGATGGTATGGTTGTTTCTGTGTAG AAACTTTTATTCT |
| M4941 (mutant) | SEQ ID NO: 54 | GATCCTTTGAATAGATTTCTATTTCCTCGGTGAGGGAA GATCTATCTGGTCTTAGAGTTGAAAAGTTACTAGACGA AAGTGGCGATGCAGTTGGAGTACGGGGAGAAGGAGCT AGAGAATTTGCAGCAGAAATATCTGTGGAAAGTTGGG GGAGAGGAGGAGGTGATGGTATGGTTGTTTCTGTGTAG AAACTTTTATTCT |
| M4942 (wildtype) | SEQ ID NO:55 | CTCAAAATwAAAAAAAGTAAAAGAGAGGTTAGAAAAA TAAGTTTTAAAAAAAGAAGTTACTTTTGTCCCTCCAAA ACTTsTTAGTAArAAATAmCAATTTCCTATTAGTTTTTCC TAArTGTGACAyGATTGTCAAGATAAGTCTmyTAAAAGG AATCmGATCTACTAGAACACAAAAAAAATTGATCTATT TTCCTAAAT |
| M4942 (mutant) | SEQ ID NO: 56 | CTCAAAATwAAAAAAAGTAAAAGAGAGGTTAGAAAAA TAAGTTTTAAAAAAAGAAGTTACTTTTGTCCCTCCAAA ACTTsTTAGTAArAAATAmCAATTTTCTATTAGTTTTTCC TAArTGTGACAyGATTGTCAAGATAAGTCTmyTAAAAGG AATCmGATCTACTAGAACACAAAAAAAATTGATCTATT TTCCTAAAT |
| M4943 (wildtype) | SEQ ID NO: 57 | rAAGTTTGAAGCCTTTAGTTTCTCATTGGTACCCGGCAT GGTAGCGTCCTGGCTTTCTGTTTTAACCATGAAGTTAG AAGTTTCArTGTTTGAAGGTCCAGCAryAGTAAACGCAC TCCCCTGTGAAAGTTTCATTTGAATTAGATCCAACAArG ACGGGCTCTTCCTTAGCACyAAACCAAGAGGACTAGGT TCATCAAG |
| M4943 (mutant) | SEQ ID NO: 58 | rAAGTTTGAAGCCTTTAGTTTCTCATTGGTACCCGGCAT GGTAGCGTCCTGGCTTTCTGTTTTAACCATGAAGTTAG AAGTTTCArTGTTTGAAGGTCCATCAryAGTAAACGCAC TCCCCTGTGAAAGTTTCATTTGAATTAGATCCAACAArG ACGGGCTCTTCCTTAGCACyAAACCAAGAGGACTAGGT TCATCAAG |
| M4945 (wildtype) | SEQ ID NO: 59 | TTGGATCCTAAAACTTGTAGAAATTAGACyCCCAAATT ATAAAAATTGAACCCTAAAACTTATACAACTCTTACAA TTTCTATAATTTTATAAGTTTAAGGGTyCAATTTTAACA CTAGTGTAAGTTTAATAGAAAATTTGAGGTTATAATTG CAACTACAACACTACTTTAAAGGTAATTTTTrmAATTTA CCCCTCyTC |
| M4945 (mutant) | SEQ ID NO: 60 | TTGGATCCTAAAACTTGTAGAAATTAGACyCCCAAATT ATAAAAATTGAACCCTAAAACTTATACAACTCTTACAA TTTCTATAATTTTATAAGTTTAAGAGTyCAATTTTAACA CTAGTGTAAGTTTAATAGAAAATTTGAGGTTATAATTG CAACTACAACACTACTTTAAAGGTAATTTTTrmAATTTA CCCCTCyTC |
| M4946 (wildtype) | SEQ ID NO: 61 | ATCATGTCAATTATTGACCAACCACCATTCGCAGTTCT AGAACAGAGAGACAyTAACAAAGAATATATTGGTTTTA GTTCATTTCCCAAGTTGAATGGAmCTTCAAACCAACGT ATrGTAGGCAATGCTGAATGTCArGTAGAAAATAAAAC AATTGAAAAATGTATGCATTGGCATTCCTTCATATTTCT TGTTAAAAAC |

TABLE 1-continued

Marker information

| Marker name | SEQ ID | Sequence |
|---|---|---|
| M4946 (mutant) | SEQ ID NO: 62 | ATCATGTCAATTATTGACCAACCACCATTCGCAGTTCT AGAACAGAGAGACAyTAACAAAGAATATATTGGTTTTA GTTCATTTCCCAAGTTGAATGGAmATTCAAACCAACGT ATrGTAGGCAATGCTGAATGTCArGTAGAAAATAAAAC AATTGAAAAATGTATGCATTGGCATTCCTTCATATTTCT TGTTAAAAAC |
| M4947 (wildtype) | SEQ ID NO: 63 | AATAAAAAwAAAwAATTCATTATATTATTTGTGCATGT GTTTAGCCGTTTATCATATATAATGATATAATTTTCATT ATTTAATAATTACTATrTyAATTGAGTTATATTAAGAAT TGTTCCAAGCAAGGTTCAAAATTCACGArCAArCTCAAG TCCAAAGAGAAAGAAGAGTCTACATAGGrGTTGCrTATC ACAAAAT |
| M4947 (mutant) | SEQ ID NO: 64 | AATAAAAAwAAAwAATTCATTATATTATTTGTGCATGT GTTTAGCCGTTTATCATATATAATGATATAATTTTCATT ATTTAATAATTACTATrTyAATTAAGTTATATTAAGAAT TGTTCCAAGCAAGGTTCAAAATTCACGArCAArCTCAAG TCCAAAGAGAAAGAAGAGTCTACATAGGrGTTGCrTATC ACAAAAT |
| M4948 (wildtype) | SEQ ID NO: 65 | TAGGCTCCCCTAAGTTGAAGAATCCmTTCTCAATCAAC GAACCTTAGGATCyCCCTAAsATCAAGAATACCTTCTTG AGTAACAAyTTAATCTCCAATACGAyCTGATACAACTC CTyGACATCAACAACACTTCCTCCrTCACAATTTCTAGG ATTAACATAGAGATCCGATCTTTCGGCCACCCCryArAC AAAATCTC |
| M4948 (mutant) | SEQ ID NO: 66 | TAGGCTCCCCTAAGTTGAAGAATCCmTTCTCAATCAAC GAACCTTAGGATCyCCCTAAsATCAAGAATACCTTCTTG AGTAACAAyTTAATCTCCAATACAAyCTGATACAACTCC TyGACATCAACAACACTTCCTCCrTCACAATTTCTAGGA TTAACATAGAGATCCGATCTTTCGGCCACCCCryArACA AAATCTC |
| M4949 (wildtype) | SEQ ID NO: 67 | GGAATGGAGAAGCCTTCATCAATACTCCTTCACTACCA TCTGATAAAGCAAAAGTTTCTTTTGAAAAAGCTAAAGT AATTAGATTAGATCGTTACAATTTCCTTAGTTCAAACA AATATTTGTCCTGTTCAGAATTTAGAATCTAAGGGwAA AAAAAAAAAAAACTTGTTTGGATCTACATTTTATTTGA TCCCTAGGTTT |
| M4949 (mutant) | SEQ ID NO: 68 | GGAATGGAGAAGCCTTCATCAATACTCCTTCACTACCA TCTGATAAAGCAAAAGTTTCTTTTGAAAAAGCTAAAGT AATTAGATTAGATCGTTACAATTTACTTAGTTCAAACA AATATTTGTCCTGTTCAGAATTTAGAATCTAAGGGwAA AAAAAAAAAAAACTTGTTTGGATCTACATTTTATTTGA TCCCTAGGTTT |
| M4950 (wildtype) | SEQ ID NO: 69 | TAAAACTAATTTTGGGkGAATTATATmAATTCAAATTT ATAAGTTAAAGATGCCAATTCACTGATGATGAAATTAC TTAATATATATATGACTTTTCCCAACCTAAGTACAACAT rGTTCAATTGGGTCAGGTTGAGTCCAAAACACACCCGTT TGAACTCATATAAAAAACCCTTAGCTTTGAAGTTTGGA TCCTTTCAA |
| M4950 (mutant) | SEQ ID NO: 70 | TAAAACTAATTTTGGGkGAATTATATmAATTCAAATTT ATAAGTTAAAGATGCCAATTCACTGATGATGAAATTAC TTAATATATATATGACTTTTCCCAGCCTAAGTACAACA TrGTTCAATTGGGTCAGGTTGAGTCCAAAACACACCCGT TTGAACTCATATAAAAAACCCTTAGCTTTGAAGTTTGG ATCCTTTCAA |
| M4951 (wildtype) | SEQ ID NO: 71 | TCAGGGAAAGTGTTCGCACACATAATAAAAAmACTTTA AAAATTTACCCTATTTTATCTATATATCTAAGCTAATAA TAATAATGGTCTkAAAAAATCTCATTTTGTTTAGTTTTA ACAGTTGTGCrTCAACTAATTCACATTTTAAAGAAATAT rTTAGAATTAATAATTATGAATTTGGAAAAAGATArTAG GTAACAA |

TABLE 1-continued

Marker information

| Marker name | SEQ ID | Sequence |
|---|---|---|
| M4951 (mutant) | SEQ ID NO: 72 | TCAGGGAAAGTGTTCGCACACATAATAAAAAmACTTTA AAAATTTACCCTATTTTATCTATATATCTAAGCTAATAA TAATAATGGTCTkAAAAAATCTCGTTTTGTTTAGTTTTA ACAGTTGTGCrTCAACTAATTCACATTTTAAAGAAATAT rTTAGAATTAATAATTATGAATTTGGAAAAAGATArTAG GTAACAA |
| M4952 (wildtype) | SEQ ID NO: 73 | GAAGAArACGCATTrCCATATAGATTGGGATTTCCTGAG TAGGTGTTAATGATGAAGAGTTCTAACTTCTAGACTAA GATGGAGAACTTATATATTTAATTGTTGTTTGGGCTTCC AGAACCTTTTAGGAATTATTAATGGAAAACAAGGrGAC CCAATGTCCATAAAGGGATATTGGACAACATATTGGAC mATGyGTAC |
| M4952 (mutant) | SEQ ID NO: 74 | GAAGAArACGCATTrCCATATAGATTGGGATTTCCTGAG TAGGTGTTAATGATGAAGAGTTCTAACTTCTAGACTAA GATGGAGAACTTATATATTTAATCGTTGTTTGGGCTTCC AGAACCTTTTAGGAATTATTAATGGAAAACAAGGrGAC CCAATGTCCATAAAGGGATATTGGACAACATATTGGAC mATGyGTAC |
| M4953 (wildtype) | SEQ ID NO:7 5 | GTAGAAGTATCTTGATATAATATAGATTTGGGGGTGTT TTAATAACTTATGCTTCAATTTTTAGATTTTGATTTCA ATTTTAATTCTATrTTCTTACTTTTGATTTTTTTGGCAsTA CTCCTTTCTTrTCACATTTCAATCTCTATTCACAAGTAGA GATGTCCrTTrAAyCCGCGGAGTCGGGGCTCTACrGGGAC CCG |
| M4953 (mutant) | SEQ ID NO: 76 | GTAGAAGTATCTTGATATAATATAGATTTGGGGGTGTT TTAATAACTTATGCTTCAATTTTTAGATTTTGATTTCA ATTTTAATTCTATrTTCTTACTTCTGATTTTTTTGGCAsTA CTCCTTTCTTrTCACATTTCAATCTCTATTCACAAGTAGA GATGTCCrTTrAAyCCGCGGAGTCGGGGCTCTACrGGGAC CCG |
| M2290 (wildtype) | SEQ ID NO: 77 | GTCATGTCGTCAATTTCTTTAATATTGTTGTGTCTACGA TTGGAAGCAAATCCAGGGTTGATTAATGAATCAAGGGT CATTTTCCGCTTCTTTCAATGATTAATTCGAATCGTTGA AATTTCTGGTGTTAATTATTTTCATTGTGCAATGTAGG TATTGTGAAACGGCAAAATCTGTTTTCAAGGATTTGCA CAAAGTTC |
| M2290 (mutant) | SEQ ID NO: 78 | GTCATGTCGTCAATTTCTTTAATATTGTTGTGTCTACGA TTGGAAGCAAATCCAGGGTTGATTAATGAATCAAGGGT CATTTTCCGCTTCTTTCAATGATGAATTCGAATCGTTGA AATTTCTGGTGTTAATTATTTTCATTGTGCAATGTAGG TATTGTGAAACGGCAAAATCTGTTTTCAAGGATTTGCA CAAAGTTC |
| M4954 (wildtype) | SEQ ID NO: 79 | TATGTTCAATGCCAAACArAACAATAAGGrAAAATGA AGGGATCTCATCmCAATTAATCTATATAGAGAAGAAAC ATTGGAAGGGTATTATTGTAATTACGTTAGGGCTTATG AAAAACTCTGCCAGCAATAAGrGCTGCTTCCATGACAA AGGAGATGACATCAATGACATCATCAACTTGGCATTTG TTCCCTTTGAA |
| M4954 (mutant) | SEQ ID NO: 80 | TATGTTCAATGCCAAACArAACAATAAGGrAAAATGA AGGGATCTCATCmCAATTAATCTATATAGAGAAGAAAC ATTGGAAGGGTATTATTGTAATTAAGTTAGGGCTTATG AAAAACTCTGCCAGCAATAAGrGCTGCTTCCATGACAA AGGAGATGACATCAATGACATCATCAACTTGGCATTTG TTCCCTTTGAA |
| M4955 (wildtype) | SEQ ID NO: 81 | AAAAAyAAAAAACAAAAAACwAAATGGTTACCATACC TAAAkAAsCAACTAATTTTAAAAATTAATCTAAAACAC ATTTTTAACACTCTATTTATAAAATTAAAAAAAyTATAA TTmTACGTGTATArCCATTCTATTACTTTCTTAGTTATTT AATTTTTTTTTTTGAGCTATTTAAAACAAACATTTTAA TTGATkTA |

TABLE 1-continued

Marker information

| Marker name | SEQ ID | Sequence |
|---|---|---|
| M4955 (mutant) | SEQ ID NO: 82 | AAAAAyAAAAAACAAAAAACwAAATGGTTACCATACC TAAAkAAsCAACTAATTTTAAAAATTAATCTAAAACAC ATTTTTAACACTCTATTTATAAAATAAAAAAAAyTATA ATTmTACGTGTATArCCATTCTATTACTTTCTTAGTTATT TAATTTTTTTTTTTGAGCTATTTAAAACAAACATTTTA ATTGATkTA |
| M4956 (wildtype) | SEQ ID NO: 83 | TCrATTTCAATGGATATTTCTGGAAAAAATAAAAAATTC AAAAAATAAAGTTAAATTAGTAAATAAACATGTwATG ATTTTTAAAAGTCTATTATTTATATCATrTTTACATTAGT TACATTTTGTTGCTTGCTTTTTTATGyTTCGTAGATTTTT CTACrATACArTTGAAATGTyrATTCACCTCTCrTGTCGAT rTCG |
| M4956 (mutant) | SEQ ID NO: 84 | TCrATTTCAATGGATATTTCTGGAAAAAATAAAAAATTC AAAAAATAAAGTTAAATTAGTAAATAAACATGTwATG ATTTTTAAAAGTCTATTATTTATAACATrTTTACATTAGT TACATTTTGTTGCTTGCTTTTTTATGyTTCGTAGATTTTT CTACrATACArTTGAAATGTyrATTCACCTCTCrTGTCGAT rTCG |
| M2296 (wildtype) | SEQ ID NO: 85 | CTGCTTCGGTCGGTTTTGACCGGTTTTCGGTTTAAGTTG ATCACTCCTAACTTTTAGTTCTCCAAGACCTTTTCAATT CCTCTCACATCCAAGATTTCGTGTCGATATTTTTTTTC AAATGTATTTGGGTACTAAATAAGTTGATTTGTTACTA ATAATTCAACTTGGCATACTATTTTTCACTACATTAAAG TTATTGA |
| M2296 (mutant) | SEQ ID NO: 86 | CTGCTTCGGTCGGTTTTGACCGGTTTTCGGTTTAAGTTG ATCACTCCTAACTTTTAGTTCTCCAAGACCTTTTCAATT CCTCTCACATCCAAGATTTCGTATCGATATTTTTTTTC AAATGTATTTGGGTACTAAATAAGTTGATTTGTTACTA ATAATTCAACTTGGCATACTATTTTTCACTACATTAAAG TTATTGA |
| M1567 (wildtype) | SEQ ID NO: 87 | TTAGCAAGAAATTAAATkAAGTyATCTCCTTATTTGAGA GAAAGAGTAGAATTAGAAAAGTGTGTACTTTATTCCAA TCACTTCTCATCACTATAAATACTAATTCTAAATGTTAA AAATAACTTAGTTTrTAACATAAAATCrACAACAAACTC TTTTTAAACGTAACTCCACAAAACTATCCATAATTACA AATATACr |
| M1567 (mutant) | SEQ ID NO: 88 | TTAGCAAGAAATTAAATkAAGTyATCTCCTTATTTGAGA GAAAGAGTAGAATTAGAAAAGTGTGTACTTTATTCCAA TCACTTCTCATCACTATAAATACCAATTCTAAATGTTAA AAATAACTTAGTTTrTAACATAAAATCrACAACAAACTC TTTTTAAACGTAACTCCACAAAACTATCCATAATTACA AATATACr |
| M2112 (wildtype) | SEQ ID NO: 89 | TATGTTACACCCAATCTTAATTTGCAATAGGAGCCCAA AGACGTGCATACATCCTAAGGGAAAGCTTTAGGCAGTA ACATTCCTCAAATGTTGACAGTATCTTGGTCTCTTTCTG TGATGATTTTCATAAAAAGTGAATTGTCTCTTGGAATCT GGGTTAAAAGGGAATATCTATTGTTCACGTATAAAACT AATCAAGGA |
| M2112 (mutant) | SEQ ID NO: 90 | TATGTTACACCCAATCTTAATTTGCAATAGGAGCCCAA AGACGTGCATACATCCTAAGGGAAAGCTTTAGGCAGTA ACATTCCTCAAATGTTGACAGTATTTTGGTCTCTTTCTG TGATGATTTTCATAAAAAGTGAATTGTCTCTTGGAATCT GGGTTAAAAGGGAATATCTATTGTTCACGTATAAAACT AATCAAGGA |
| M2115 (wildtype) | SEQ ID NO: 91 | ATCTGACCTTTTAATAGGTGACATATATTTAATAAGTTG AATTATGTTCAAGTTGGTGTTAAACATTTAAACTAAGG TTTAATGCATTTTAGATTCTTTGATGAGAAATAACCATT TTAAGTGAAAACTTTCCTTTAAAATTAACTTTCTAATTA AAAAAATCTAAAAGAATTAATTTCATTTAGTTGATTTT AATAATTT |

TABLE 1-continued

Marker information

| Marker name | SEQ ID | Sequence |
|---|---|---|
| M2115 (mutant) | SEQ ID NO: 92 | ATCTGACCTTTTAATAGGTGACATATATTTAATAAGTTG AATTATGTTCAAGTTGGTGTTAAACATTTAAACTAAGG TTTAATGCATTTTAGATTCTTTGCTGAGAAATAACCATT TTAAGTGAAAACTTTCCTTTAAAATTAACTTTCTAATTA AAAAAATCTAAAAGAATTAATTTCATTTAGTTGATTTT AATAATTT |
| M2116 (wildtype) | SEQ ID NO: 93 | CATTTCAACCTCTAAGCCAATAAAACATCTTATTTAAC CAAAAAATTTTATTTTGAAATGAATAAACAAAGCATCT CGAAGACTATTAATCTCAACTCTATCATCACCCGTTAT GATCATGTCATCAACATAGAGTAGAAGTATTATATATT TTGAGGTTGTCATTGAAACAGACTTAAATATGCATTTG AAGATTTGAAA |
| M2116 (mutant) | SEQ ID NO: 94 | CATTTCAACCTCTAAGCCAATAAAACATCTTATTTAAC CAAAAAATTTTATTTTGAAATGAATAAACAAAGCATCT CGAAGACTATTAATCTCAACTCTACCATCACCCGTTAT GATCATGTCATCAACATAGAGTAGAAGTATTATATATT TTGAGGTTGTCATTGAAACAGACTTAAATATGCATTTG AAGATTTGAAA |
| M2118 (wildtype) | SEQ ID NO: 95 | CTAATTTCAACCTTTCCAAACTATCAAAAGGGATTGAC ATGATATTAATAATTAAGATCATATGCTTTAAGCTACTT TGTTTGGTTGGTAAAAATGAGATGCATTTATTCAATCA AGTTATTATATTAATTTAATTTCCTTAGTGGGTTTGGTT TGGTGCCTTAAATATTTACTAACCAAAACCCTTATCAA ATTACTGTC |
| M2118 (mutant) | SEQ ID NO: 96 | CTAATTTCAACCTTTCCAAACTATCAAAAGGGATTGAC ATGATATTAATAATTAAGATCATATGCTTTAAGCTACTT TGTTTGGTTGGTAAAAATGAGATTCATTTATTCAATCA AGTTATTATATTAATTTAATTTCCTTAGTGGGTTTGGTT TGGTGCCTTAAATATTTACTAACCAAAACCCTTATCAA ATTACTGTC |
| M2122 (wildtype) | SEQ ID NO: 97 | AACTTCAATGTTCTGAATCTGGAAAAACTAAGTTTAAT GGACCTTAGATGGTGAAAAAAAAAAAAAAAAAAAAA ATTCAAAACATGCAGTTGGTTTCCGCCACTGACAAATT TCAGACCTTAGAAAACTGAAGCCAAGCTCATAAAATAT TTGGAAAATAAATGGTACAAACAATGGTGGAGACTCTT CAACTGAGTTTT |
| M2122 (mutant) | SEQ ID NO: 98 | AACTTCAATGTTCTGAATCTGGAAAAACTAAGTTTAAT GGACCTTAGATGGTGAAAAAAAAAAAAAAAAAAAAA ATTCAAAACATGCAGTTGGTTTCCGTCACTGACAAATT TCAGACCTTAGAAAACTGAAGCCAAGCTCATAAAATAT TTGGAAAATAAATGGTACAAACAATGGTGGAGACTCTT CAACTGAGTTTT |

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Resistance Assay ZYMV

A watermelon population, made by crossing a wild watermelon accession with an internal line was phenotyped on the presence of resistance to ZYMV. The plants of the population were inoculated with ZYMV. The ZYMV inoculum is prepared by grinding young watermelon plant leaves that show heavy symptoms, mixing the grinded leaves with a buffer and carborundum and charcoal.

Meanwhile, seeds of different watermelon plant lines are sown, transplanted once they have germinated and then grown in a greenhouse for around 4 weeks until they reach the 5/6 leaves stage. Plants are then inoculated by hand with the mixture described above. Two leaves per plant are inoculated. One plant per line is not inoculated and is kept as a control. After 3 to 4 days the inoculation is repeated. Plants are incubated in a climate cell and after a few days they are put in a greenhouse.

After 12, 14 and 20 days following the first inoculation, the plants were phenotyped and the level of the infection was visually assessed according to a semi-quantitative scale:
 1. no symptoms
 2. no symptoms to some chlorotic lesions on the old leaves
 3. some chlorotic lesions on the old leaves
 4. some chlorotic lesions on the old leaves to more chlorotic lesions on the old leaves
 5. more chlorotic lesions on all the leaves
 6. more chlorotic lesions to obvious mosaic and deformations on the young leaves 7. obvious mosaic and deformations on the young leaves
8. obvious mosaic and deformations on the young leaves to strong stunting and mosaic with deformations
9. strong stunting and mosaic with deformations.

Scores 7 and higher are considered to be susceptible.

Example 2: Resistance Assay WMV

A watermelon population was phenotyped on the presence of resistance to WMV. The plants of the population were inoculated with WMV. The WMV inoculum is prepared by grinding young watermelon plant leaves that show heavy symptoms, mixing the grinded leaves with a buffer and carborundrum and charcoal.

Meanwhile, seeds of different watermelon plant lines are sown, transplanted once they have germinated and then grown in a greenhouse for around 4 weeks until they reach the 5/6 leaves stage. Plants are then inoculated by hand with the mixture described above. Two leaves per plant are inoculated. After 3 to 4 days the inoculation is repeated. Plants are incubated in a climate cell and after a few days they are put in a greenhouse.

After 11, 17 and 24 days following the first inoculation, the plants were phenotyped and the level of infection was visually assessed, according to a semi-quantitative scale:
1. No symptoms
2. No symptoms to some discolourations on the old leaves
3. Some discolourations on the old leaves
4. Some discolourations on the old leaves to some discolourations and growth reduction
5. Some discolourations and growth reduction
6. Some discolouration and growth reduction to obvious mosaic and deformations on the young leaves
7. Obvious mosaic and deformations on the young leaves
8. Obvious mosaic and deformations on the young leaves to strong stunting and mosaic with deformations
9. Strong stunting and mosaic with deformations.

Scores 7 and higher are considered to be susceptible.

Example 3: Identifying ZYMV Resistance in a Watermelon Plant and Finding QTLs

A watermelon population was made by crossing a parent line resistant to ZYMV with a parent line susceptible to ZYMV. The parent lines and the plants of the F1 were genotyped with SNP markers. The populations were analysed for the presence of QTLs linked to ZYMV resistance.

The plants were tested for resistance against ZYMV according to the method as described in Example 1. The population consisted of 149 plant lines plants, and of each line 2-4 plants were used for the phenotypic analysis. Using phenotypic data on ZYMV resistance combined with SNP markers, two QTLs were found: a QTL on chromosome 8, with an explained variance of 28.6% (LOD 12.8); and a QTL on chromosome 3 with an explained variance of 15.9% (LOD 7.73). The QTL on chromosome 3, designated here as QTL3, explains 15.9%. The QTL3 on chromosome 3 coincides with the previously reported eIF4e, the eukaryotic initiation factor in watermelon, that is known to be associated with resistance to ZYMV. Surprisingly, the newly found QTL1 on chromosome 8 explains more of the variance found in ZYMV resistance than the known gene on chromosome 3. The LOD score, which means "the log of odds ratio", or the $\log_{10}$ likelihood ratio, compares the hypothesis that there is a QTL at the selected marker with the hypothesis that there is no QTL anywhere in the genome. The higher the LOD score, the more evidence to support the presence of a QTL.

Example 4: Identifying ZYMV Resistance in a Watermelon Plant and Finding QTLs

A watermelon population was made by crossing a parent line resistant to WMV with a parent line susceptible to WMV. The parent lines and the plants of the F1 were genotyped with SNP markers. The populations were analyzed for the presence of QTLs linked to WMV resistance. In this population, a QTL was found that was linked to resistance against WMV. The plants were tested for resistance against WMV according to the method as described in Example 1. The population consisted of 149 plant lines plants, and of each line 2-4 plants were used for the phenotypic analysis. Using phenotypic data on WMV resistance combined with informative markers, three QTLs were found: a QTL on chromosome 8, designated as QTL1, with an explained variance of 32.5% (LOD 15.7); a QTL on chromosome 6, designated as QTL2, with an explained variance of 6.8% (LOD 4.7) and a QTL on chromosome 3, designated as QTL3, with an explained variance of 16% (LOD 9.0). The QTL on chromosome 3 coincides with the QTL3 found for ZYMV, and coincides with the previously reported eIF4e, the eukaryotic transcription initiation factor in watermelon.

Example 5: Validation of Individual QTLs and Combination of QTLs

To validate the effect that the QTLs individually and in combination have on the resistance against potyviruses in watermelon plants as described in Example 3 and Example 4, crossings were made between internal watermelon plant lines containing one or more of QTL1, QTL2 and QTL3 and a watermelon plant line not containing the said QTLs. Plants from the F6 population that originated from this cross were tested for the presence of one or more of QTL1, QTL2 and QTL3 with markers sequences SEQ ID NO:4-42, SEQ ID NO:46-86, SEQ ID NO:92-96 as shown in Table 1.

In FIG. 1, the average ZYMV resistance scores for plants from the F6 with and without one or more of QTL1, QTL2, QTL3 are given.

As shown in FIG. 1, The average resistance score of watermelon plants having none of the QTLs is 7.7 on a scale 0 to 9. The average resistance score of watermelon plants comprising the QTL1 is 5.8. The average resistance score of watermelon plants comprising the QTL2 is 3.1. The average resistance score of watermelon plants comprising the QTL3 is 6.0. Watermelon plants comprising QTL1 and QTL2 score on average 4.2. Watermelon plants comprising both QTL1 and QTL3 score on average 2.5. Watermelon plants comprising both QTL2 and QTL3 score on average 3.9. Watermelon plants that may comprise the resistance conferring alleles of both QTL1 and QTL3 show the best resistance to ZYMV, followed by plants comprising the resistance conferring allele of QTL2 and hereafter followed by plants comprising the resistance conferring alleles of QTL2 and QTL3.

Figure 2:
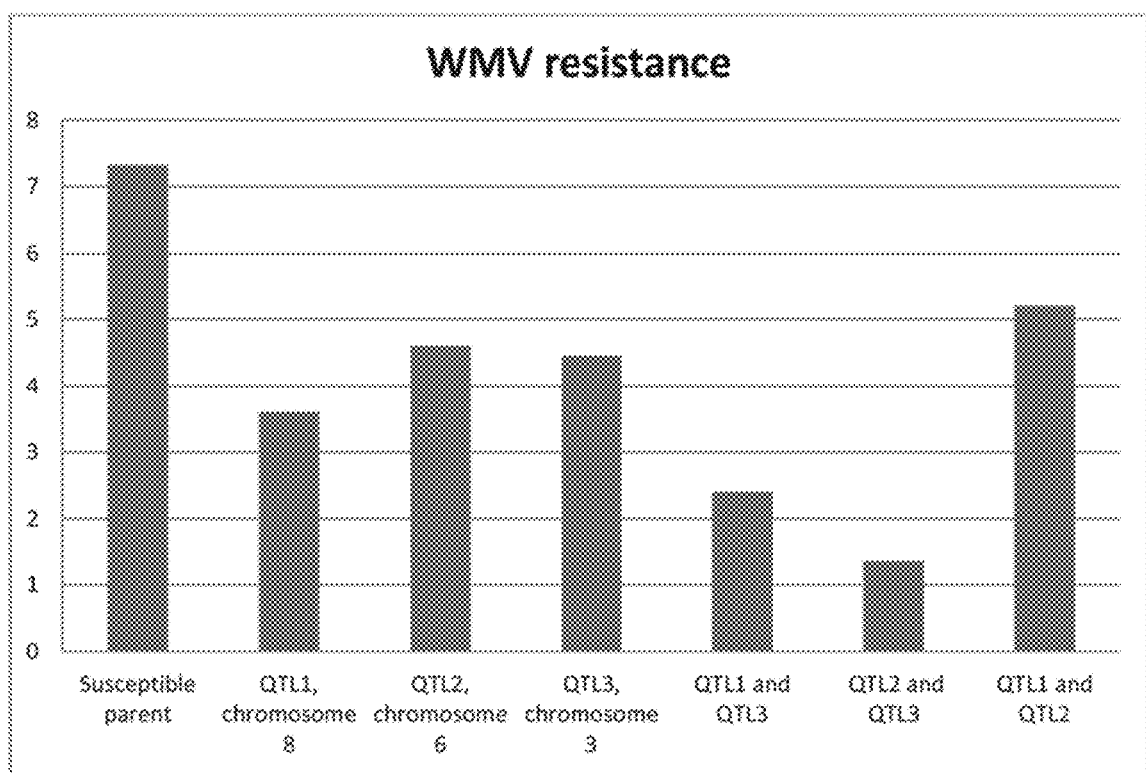
FIG. 2. Graphs showing the differences in WMV resistance of watermelon plants which may comprise the potyvirus resistance conferring alleles of QTL1 and/or QTL2 and/or QTL3, separately or in combination.

In FIG. 2, the average WMV resistance scores for watermelon plants from the F6 with and without one or more of QTL1, QTL2 and QTL3 are given.

As shown in FIG. 2, the average resistance score of watermelon plants having none of the QTLs is 7.3 on a scale 0 to 9. The average score of watermelon plants comprising the QTL1 is 3.6. The average score of watermelon plants comprising the QTL2 is 4.6. The average score of watermelon plants comprising the QTL3 is 4.5. Watermelon plants comprising QTL1 and QTL2 score on average 5.2. Watermelon plants comprising both QTL1 and QTL3 score on average 2.4. Watermelon plants comprising both QTL2 and QTL3 score on average 1.4.

The invention is further described by the following numbered paragraphs:

1. A watermelon plant of the species *Citrullus lanatus* subsp. *lanatus* that produces fruits with red flesh and comprises a QTL1 located on chromosome 8, and/or a QTL2 located on chromosome 6, which QTLs confer resistance to a potyvirus and wherein QTL1 is as found in a watermelon plant, representative seed of which was deposited under deposit number NCIMB 42537, and wherein QTL1 is located between molecular markers M2382 (represented by SEQ ID NO:1 and/or SEQ ID NO:2) and M2386 (represented by SEQ ID NO:41 and/or SEQ ID NO:42), and wherein QTL2 is as found in a watermelon plant, representative seed of which was deposited under deposit number NCIMB 42536, and wherein QTL2 is located between molecular markers M2283 (represented by SEQ ID NO:43 and/or SEQ ID NO:44) and M1567 (represented by SEQ ID NO:87 and/or SEQ ID NO:88).

2. The watermelon plant of paragraph 1, wherein the mature fruits of said plant have flesh with soluble solids of at least 5.0 brix, preferably at least 5.5 brix, more preferably at least 6.0 brix.

3. The watermelon plant of paragraph 1 or 2, wherein in the seeds of deposit NCIMB 42537 QTL1 is linked to a marker sequence selected from the group consisting of SEQ ID NO:4 (M4996), SEQ ID NO:6 (M4997), SEQ ID NO:8 (M4998), SEQ ID NO:10 (M4999), SEQ ID NO:12 (M5000), SEQ ID NO:14 (M5001); SEQ ID NO:16 (M5003), SEQ ID NO:18 (M2384), SEQ ID NO:20 (M5004), SEQ ID NO:22 (M5005), SEQ ID NO:24 (M5007), SEQ ID NO:26 (M5008), SEQ ID NO:28 (M5010), SEQ ID NO:30 (M5011), SEQ ID NO:32 (M5012), SEQ ID NO:34 M5014), SEQ ID NO:36 (M5015), SEQ ID NO:38 (M5016) and SEQ ID NO:40 (M5017) and wherein in the seeds of deposit NCIMB 42536 and deposit NCIMB 42538 QTL2 is linked to a marker selected from the group consisting of SEQ ID NO:46 (M2285), SEQ ID NO:48 (M4938), SEQ ID NO:50 (M4939), SEQ ID NO:52 (M4940), SEQ ID NO:54 (M4941), SEQ ID NO:56 (M4941), SEQ ID NO:58 (M4943), SEQ ID NO:60 (M4945), SEQ ID NO:62 (M4946), SEQ ID NO:64 (M4947), SEQ ID NO:66 (M4948), SEQ ID NO:68 (M4949), SEQ ID NO: 70 (M4950), SEQ ID NO:72 M4951), SEQ ID NO:74 (M4952), SEQ ID NO:76 (M4953), SEQ ID NO:78 (M2290), SEQ ID NO:80 (M4954), SEQ ID NO:82 (M4955), SEQ ID NO:84 (M4956) and SEQ ID NO:86 M2296).

4. The watermelon plant of any of the paragraphs 1 to 3, wherein the watermelon plant further comprises a QTL3 located on chromosome 3, which confers resistance to a potyvirus, wherein QTL3 is as found in a watermelon plant, representative seed of which was deposited under deposit accession number NCIMB 42535, and wherein QTL3 is located between molecular markers M2112 (represented by SEQ ID NO:89 or SEQ ID NO:90) and M2122 (represented by SEQ ID NO:97 or SEQ ID NO:98).

5. The watermelon plant of paragraph 4, wherein in the seeds of deposit NCIMB 42535 the QTL3 is linked to a marker sequence selected from the group consisting of SEQ ID NO:92 (M2115), SEQ ID NO:94 (M2116) and SEQ ID NO:96 (M2118).

6. The watermelon plant of paragraph 4 or 5, wherein QTL3 comprises the resistance conferring allele of the watermelon eukaryotic translation initiation factor eIF4E gene.

7. The watermelon plant of any one of the paragraphs 1-6, wherein the watermelon plant shows resistance to ZYMV and/or WMV.

8. Seed capable of growing into a watermelon plant of any one of the paragraphs 1-7.

9. Seed of a watermelon plant of any one of the paragraphs 1-7, wherein the seed comprises QTL1 and/or QTL2 and/or QTL3.

10. Propagation material capable of developing into and/or being derived from a plant of any one of the paragraphs 1-7, wherein the propagation material is selected from a microspore, pollen, ovary, ovule, embryo, embryo sac, egg cell, cutting, root, hypocotyl, cotyledon, stem, leaf, flower, anther, seed, meristematic cell, protoplast, cell, or tissue culture thereof and wherein the propagation material comprises QTL1 and/or QTL2 and/or QTL3.

11. A method of selecting a watermelon plant that comprises QTL1, and/or QTL2 and/or QTL3, comprising detecting a marker sequence selected from the group consisting of SEQ ID NO:4, SEQ ID NO:6, SEQ ID NO:8, SEQ ID NO:10, SEQ ID NO:12, SEQ ID NO:14; SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:92, SEQ ID NO:94 and SEQ ID NO:96 in the genome of watermelon plants and selecting a watermelon plant that comprises the marker sequence as a watermelon plant comprising QTL1, and/or QTL2 and/or QTL3.

12. The method of paragraph 11, wherein a watermelon plant comprising QTL1, and/or QTL2 and optionally QTL3 is selected and a phenotypical assay for ZYMV resistance is performed, to select a watermelon plant resistant to ZYMV.

13. The method of paragraph 11, further comprising performing a phenotypical assay for WMV resistance, to select a watermelon plant resistant to WMV.

14. Use of QTL1 and/or QTL2, as defined in any one of the paragraphs 1-3, and/or QTL3 as defined in any one of the paragraphs 4-6, for identifying and/or developing a watermelon plant showing resistance to a potyvirus.

15. The use of paragraph 14, wherein the watermelon plant shows resistance to ZYMV and/or WMV.

16. A marker selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40; or a marker derived therefrom, which marker is linked to QTL1.

17. A marker selected from the group consisting of SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86 or a marker derived therefrom, which marker is linked to QTL2.

18. A marker selected from the group consisting of SEQ ID NO:92, SEQ ID NO:94, SEQ ID NO:96 or a marker derived therefrom, which marker is linked to QTL3.

19. Set of markers, which comprises two or more markers selected from the group consisting of the markers of paragraph 16, the markers of paragraph 17 and the markers of paragraph 18.

20. Use of a marker or marker set as defined in any one of the paragraphs 16-19 for identifying a watermelon plant comprising one or more of QTL1, QTL2 and QTL3.

21. A method for producing a watermelon plant which shows resistance to a potyvirus, said method comprising:

a) crossing a plant of any one of the paragraphs 1-7 with another plant to obtain an F1 population;

b) optionally performing one or more rounds of selfing and/or crossing a plant from the F1 to obtain a further generation population;

c) selecting from the population a plant that comprises QTL1 and/or QTL2 and/or QTL3 and shows resistance to a potyvirus.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A watermelon plant of the species *Citrullus lanatus* subsp. *lanatus* that produces fruits with red flesh and comprises
   a) a QTL3 located on chromosome 3, which confers resistance to a potyvirus, wherein QTL3 is as found in a watermelon plant, representative seed of which was deposited under deposit accession number NCIMB 42535, and wherein QTL3 is located between molecular marker M2112, having SEQ ID NO:89 or SEQ ID NO:90, and molecular marker M2122, having SEQ ID NO:97 or SEQ ID NO:98, and is linked to the SNP at position 101 of SEQ ID NO:94 of molecular marker M2116, and
   b)i) QTL1, or
   b)ii) QTL2, or
   b)iii) QTL1 and QTL2, wherein:
   QTL1 located on chromosome 8,
   QTL2 located on chromosome 6,
   each of QTL1 and QTL2 confer resistance to a potyvirus,
   QTL1 is as found in a watermelon plant, representative seed of which was deposited under deposit number NCIMB 42537, and wherein QTL1 is located between molecular marker M2382, having SEQ ID NO:1 or SEQ ID NO:2, and molecular marker M2386, having SEQ ID NO:41 or SEQ ID NO:42, and is linked to the SNP at position 101 of SEQ ID NO:18 of molecular marker M2384, and
   QTL2 is as found in a watermelon plant, representative seed of which was deposited under deposit number NCIMB 42536, and wherein QTL2 is located between molecular marker M2283, having SEQ ID NO:43 or SEQ ID NO:44, and molecular marker M1567, having SEQ ID NO:87 or SEQ ID NO:88 and is linked to the SNP at position 101 of SEQ ID NO:74 of molecular marker M4952.

2. The watermelon plant as claimed in claim 1, wherein the mature fruits of said plant have flesh with soluble solids of at least 5.0 brix, preferably at least 5.5 brix, more preferably at least 6.0 brix.

3. The watermelon plant as claimed in claim 1, wherein in the seeds of deposit NCIMB 42537 QTL1 is furthermore linked to the SNP at position 101 of SEQ ID NO:4 of molecular marker M4996, SEQ ID NO:6 of molecular marker M4997, SEQ ID NO:8 of molecular marker M4998, SEQ ID NO:10 of molecular marker M4999, SEQ ID NO:12 of molecular marker M5000, SEQ ID NO:14 of molecular marker M5001; SEQ ID NO:16 of molecular marker M5003, SEQ ID NO:20 of molecular marker M5004, SEQ ID NO:22 of molecular marker M5005, SEQ ID NO:24 of molecular marker M5007, SEQ ID NO:26 of molecular marker M5008, SEQ ID NO:28 of molecular marker M5010, SEQ ID NO:30 of molecular marker M5011, SEQ ID NO:32 of molecular marker M5012, SEQ ID NO:34 of molecular marker M5014, SEQ ID NO:36 of molecular marker M5015, SEQ ID NO:38 of molecular marker M5016 or SEQ ID NO:40 of molecular marker M5017 and wherein in the seeds of deposit NCIMB 42536 QTL2 is furthermore linked to the SNP at position 101 of SEQ ID NO:46 of molecular marker M2285, SEQ ID NO:48 of molecular marker M4938, SEQ ID NO:50 of molecular marker M4939, SEQ ID NO:52 of molecular marker M4940, SEQ ID NO:54 of molecular marker M4941, SEQ ID NO:56 of molecular marker M4941, SEQ ID NO:58 of molecular marker M4943, SEQ ID NO:60 of molecular marker M4945, SEQ ID NO:62 of molecular marker M4946, SEQ ID NO:64 of molecular marker M4947, SEQ ID NO:66 of molecular marker M4948, SEQ ID NO:68 of molecular marker M4949, SEQ ID NO: 70 of molecular marker M4950, SEQ ID NO:72 of molecular marker M4951, SEQ ID NO:76 of molecular marker M4953, SEQ ID NO:78 of molecular marker M2290, SEQ ID NO:80 of molecular marker M4954, or SEQ ID NO:82 of molecular marker M4955.

4. The watermelon plant as claimed in claim 1, wherein in the seeds of deposit NCIMB 42535 QTL3 is furthermore linked to the SNP at position 101 of SEQ ID NO:92 of molecular marker M2115 or SEQ ID NO:96 of molecular marker M2118.

5. The watermelon plant as claimed in claim 1, wherein QTL3 comprises the resistance conferring allele of the watermelon eukaryotic translation initiation factor eIF4E gene.

6. The watermelon plant as claimed in claim 1, wherein the watermelon plant shows resistance to ZYMV and/or WMV.

7. A seed capable of growing into a watermelon plant as claimed in claim 1.

8. A seed of the watermelon plant as claimed in claim 1, wherein the seed comprises QTL3.

9. A propagation material capable of developing into and/or being derived from a plant as claimed in claim 1, wherein the propagation material is selected from a microspore, pollen, ovary, ovule, embryo, embryo sac, egg cell, cutting, root, hypocotyl, cotyledon, stem, leaf, flower, anther, seed, meristematic cell, protoplast, cell, or tissue culture thereof and wherein the propagation material comprises QTL3.

10. A method of selecting a watermelon plant that comprises QTL1, and/or QTL2 and/or QTL3, comprising detecting a marker sequence selected from the group consisting of SEQ ID NO:4, SEQ ID NO:6, SEQ ID NO:8, SEQ ID NO:10, SEQ ID NO:12, SEQ ID NO:14; SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:92, SEQ ID NO:94 and SEQ ID NO:96 in the genome of watermelon plants and selecting a watermelon plant that comprises the marker sequence as a watermelon plant comprising QTL1, and/or QTL2 and/or QTL3.

11. The method of claim 10, further comprising performing a phenotypical assay for ZYMV resistance to select a watermelon plant resistant to ZYMV.

12. The method of claim 10, further comprising performing a phenotypical assay for WMV resistance, to select a watermelon plant resistant to WMV.

13. A method for producing a watermelon plant which shows resistance to a potyvirus, said method comprising:
   a) crossing a plant as claimed in claim 1 with another plant to obtain an F1 population;
   b) optionally performing one or more rounds of selfing and/or crossing a plant from the F1 to obtain a further generation population;
   c) selecting from the population a plant that comprises QTL3 and shows resistance to a potyvirus.

\* \* \* \* \*

SEQUENCE LISTING

```
<160> NUMBER OF SEQ ID NOS: 98

<210> SEQ ID NO 1
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 1
caaatagata tgggacttga atatctagat acatggattt taattttaaa aataaaataa      60
aaaagagaag ttattataaa tagaaaaaat atcaaactaa ctacaaatat aaaaaaactt     120
ttactgtcta ttagcgatag aacgcgatag acttctatca catgagcgat attgagcaat     180
ggacttctgt cagtctatcg c                                                201

<210> SEQ ID NO 2
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 2
caaatagata tgggacttga atatctagat acatggattt taattttaaa aataaaataa      60
aaaagagaag ttattataaa tagaaaaaat atcaaactaa ttcaaatat aaaaaaactt      120 ttactgtcta ttagcgatag aacgcgatag acttctatca catgagcgat attgagcaat     180
ggacttctgt cagtctatcg c                                                201

<210> SEQ ID NO 3
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 3
tgtaaagaag atatgtaaag gtacacgaag agcttcagca acatgtgtat gtcctgcaac      60
```

```
ccaaatcaaa caagcacagt gtgaaatttg aaaactaacc cttcaataga agttctattc    120
casccattca attaawaatt tagtaaacaa ttatrtgaat caaatgttta atgatagact    180
ttattgtggg aaattgcctg c                                             201

<210> SEQ ID NO 4
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 4
tgtaaagaag atatgtaaag gtacacgaag agcttcagca acatgtgtat gtcctgcaac     60
ccaaatcaaa caagcacagt gtgaaatttg aaaactaacc gttcaataga agttctattc    120
casccattca attaawaatt tagtaaacaa ttatrtgaat caaatgttta atgatagact    180
ttattgtggg aaattgcctg c                                             201

<210> SEQ ID NO 5
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 5
tttgaagtga caatatttat catttgtgga tttaatctcy acgattatat tgttagttcc     60
aatatatata taacccttgc atgttggaga wtggtgaggc graggctttt cttagggaga    120
ctggtacccc aacaaactct tcttttcccc ttgcccccat tatctcttgt tggtccmcat    180
ttgttgccgc taacrgaaag t                                             201

<210> SEQ ID NO 6
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 6
tttgaagtga caatatttat catttgtgga tttaatctcy acgattatat tgttagttcc     60
aatatatata taacccttgc atgttggaga wtggtgaggc araggctttt cttagggaga    120
ctggtacccc aacaaactct tcttttcccc ttgcccccat tatctcttgt tggtccmcat    180
ttgttgccgc taacrgaaag t                                             201

<210> SEQ ID NO 7
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"
```

<400> SEQUENCE: 7
agattgagtt ataattttct ggtggttaat catacagtgt aagcttcaat tgagtcgtga    60
acttcatttt actactaatg agctatatgt atcgtctttg attctggatw agcatgaaag   120 cttctcttcat gttaaatcac aaactaaatg gtttttkatt atgatcaggt ggcaaaaaac  180
tattaacacc tcagcctcgg t                                            201

<210> SEQ ID NO 8
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 8
agattgagtt ataattttct ggtggttaat catacagtgt aagcttcaat tgagtcgtga    60
acttcatttt actactaatg agctatatgt atcgtctttg gttctggatw agcatgaaag   120 cttctcttcat gttaaatcac aaactaaatg gtttttkatt atgatcaggt ggcaaaaaac  180
tattaacacc tcagcctcgg t                                            201

<210> SEQ ID NO 9
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 9
aggtcctcac caatatccag atcatcttca acctttgaac gtggatcccc gcccgaatca    60
tcttgttcag ctgcacccgt cccacgtaaa ggaggagggg ccagaggcgg cagtacctcy   120
tcttgtacaa aggcccgaaa gttgttcttt gagggmtttr cttttgagca aaatacttcc   180
agraaattat tcagacaacc t                                            201

<210> SEQ ID NO 10
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 10
aggtcctcac caatatccag atcatcttca acctttgaac gtggatcccc gcccgaatca    60
tcttgttcag ctgcacccgt cccacgtaaa ggaggagggg gcagaggcgg cagtacctcy   120
tcttgtacaa aggcccgaaa gttgttcttt gagggmtttr cttttgagca aaatacttcc   180
agraaattat tcagacaacc t                                            201

<210> SEQ ID NO 11
<211> LENGTH: 201
<212> TYPE: DNA
<213> ORGANISM: Citrullus lanatus

```
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 11
tatccattac ttcagcgaac cgccatttca ttgttttat cccatggctt tgtcttcgtt      60
tcycatttct tcctctgtaa cgattcgatt agcacccraa tacaattcga ttgcgatttc    120
gttcatcgag ycccaaacat gaggtatacc tatcgcttct tgattctttt cgtttcttgt    180
tctatacaaa acgatgagga a                                              201

<210> SEQ ID NO 12
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 12
tatccattac ttcagcgaac cgccatttca ttgttttat cccatggctt tgtcttcgtt      60
tcycatttct tcctctgtaa cgattcgatt agcacccraa cacaattcga ttgcgatttc    120
gttcatcgag ycccaaacat gaggtatacc tatcgcttct tgattctttt cgtttcttgt    180
tctatacaaa acgatgagga a                                              201

<210> SEQ ID NO 13
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 13 atttttgtc trtttctttt tctgtgttyt gtttcgtgct ttaggctaaa yttatttgtt      60
ttttacttgc agtgatagat ggctgaccta aaaattaagg ctgagaatcg ttttacagt    120 taagctwcra gcctctcatc tcacatcgga ttgcaaatag rataatcaaa gagaagcttr    180
cagagagaca acttcaattg t                                              201

<210> SEQ ID NO 14
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 14 atttttgtc trtttctttt tctgtgttyt gtttcgtgct ttaggctaaa yttatttgtt      60
ttttacttgc agtgatagat ggctgaccta aaaattaagg ttgagaatcg ttttacagt    120 taagctwcra gcctctcatc tcacatcgga ttgcaaatag rataatcaaa gagaagcttr    180
cagagagaca acttcaattg t                                              201
```

<210> SEQ ID NO 15
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 15
tgatttaatt takattatca atttatgcat arttactaaa ktaagctaac atgtatttyc      60
tcttttgaag ttggaggttc aattctccct ctcctaayta ttgtactaaa aaaaaatwat     120
accatcatct tamaatarag aaaaattgta attgaatagt tataaataaa ataaaaggtt     180
aaaatatcct ttcacaaagt t                                               201

<210> SEQ ID NO 16
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 16
tgatttaatt takattatca atttatgcat arttactaaa ktaagctaac atgtatttyc      60
tcttttgaag ttggaggttc aattctccct ctcctaayta gtgtactaaa aaaaaatwat     120
accatcatct tamaatarag aaaaattgta attgaatagt tataaataaa ataaaaggtt     180
aaaatatcct ttcacaaagt t                                               201

<210> SEQ ID NO 17
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 17
acaagctctt catgtaacca atttctggtg gtattgtgcc agagagactg ttgcaactca      60
aatcaagtag agttagtttc tccaggttct taatagactt cgggattgac cctgtcagta    120
gattattatt gagtataagt ttattcaaat aactgaaatt tccaaagctc tgaggaattt    180
caccagtgaa gctgtttcga c                                              201

<210> SEQ ID NO 18
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 18
acaagctctt catgtaacca atttctggtg gtattgtgcc agagagactg ttgcaactca      60
aatcaagtag agttagtttc tccaggttct taatagactt tgggattgac cctgtcagta    120
gattattatt gagtataagt ttattcaaat aactgaaatt tccaaagctc tgaggaattt    180
caccagtgaa gctgtttcga c                                              201

<210> SEQ ID NO 19
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 19
graagaaatt ttatttttttt taaaaaaaaa tgattctatc cattttccag tcaactttac    60
ggaaawttgt acataatcat ttcttttcct tcyttttttt ttttyttttc aagaagacaa   120
ctatttccct ycaagttwtg aggttatttt ttataaagtt gactggagaa tactattttc   180
ctaagaattc caatcaatct a                                             201

<210> SEQ ID NO 20
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 20
graagaaatt ttatttttttt taaaaaaaaa tgattctatc cattttccag tcaactttac    60
ggaaawttgt acataatcat ttcttttcct tcyttttttt cttttytttc aagaagacaa   120
ctatttccct ycaagttwtg aggttatttt ttataaagtt gactggagaa tactattttc   180
ctaagaattc caatcaatct a                                             201

<210> SEQ ID NO 21
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 21
aaaagaagaa gaagaaaaaa aaactactt ctttaattg ataataaaat aaaagaaat    60 ttaagagtga araagatatt tatagtctta atttaaaaaa gaawwaaaar waaaaaawaa   120
aatggttact ttaacggacc aacatyycta acatatacaa taattaaaaa ratatatgta   180
tagtaargtt aaaaaawgtc t                                             201

<210> SEQ ID NO 22
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 22

```
aaaagaagaa gaagaaaaaa aaactacttt cttttaattg ataataaaat aaaaagaaat    60
ttaagagtga araagatatt tatagtctta atttaaaaaa aaawwaaaar waaaaaawaa   120
aatggttact ttaacggacc aacatyycta acatatacaa taattaaaaa ratatatgta   180
tagtaargtt aaaaaawgtc t                                              201
```

<210> SEQ ID NO 23
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 23

```
ggaaatatta gagggaggaa raaataaaga rraaaagatt gartactaty kaatttgagt    60
tatttaacac cgacttatga agttggtaas ctaataccyt ttaaaatttt aaaatrtttc   120
attttaaaag tataaataat agatttagaa gatacttttg aatgttaaca tsacatttta   180
aawtttaaat aataatygaa g                                              201
```

<210> SEQ ID NO 24
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 24

```
ggaaatatta gagggaggaa raaataaaga rraaaagatt gartactaty kaatttgagt    60
tatttaacac cgacttatga agttggtaas ctaataccyt ctaaaatttt aaaatrtttc   120
attttaaaag tataaataat agatttagaa gatacttttg aatgttaaca tsacatttta   180
aawtttaaat aataatygaa g                                              201
```

<210> SEQ ID NO 25
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 25

```
gaaaaagatt gtgataatag traacagtaa aattagtcak gtatktggac ataggyggta    60
gacttcaatt tgtgttttta aacgaartttt taattatact tttgtaggtt taaagttctt   120
ttttaattat cattattact ctraaattac caraaaaacg acattttgct cmtttctact   180
aaaataaaga raatatmatt g                                              201
```

<210> SEQ ID NO 26
<211> LENGTH: 201
<212> TYPE: DNA
<213> ORGANISM: Citrullus lanatus
<220> FEATURE:

```
<221> NAME/KEY: source
<222> LOCATION: 1..201
<223> OTHER INFORMATION: /organism="Citrullus lanatus"
      /mol_type="unassigned DNA"

<400> SEQUENCE: 26
gaaaaagatt gtgataatag traacagtaa aattagtcak gtatktggac ataggyggta      60
gacttcaatt tgtgttttta aacgaarttt taattatact cttgtaggtt taaagttctt     120
ttttaattat cattattact ctraaattac caraaaaacg acattttgct cmtttctact    180
aaaataaaga raatatmatt g                                               201

<210> SEQ ID NO 27
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 27
aaagactata aaakagcact tatatatatt ttccattttt cttraakgat gmtraaaaga     60
tgttaatcta gttgagrtgt tcrtccrcac tactcttaty ccaycatcct tagtattttg    120
ttaaaaaaaa aaraaaaaak awtcttcatt tttaactctt tgatgatst agtaattggt    180 attgtaaaat gttcttgaaa t                                               201

<210> SEQ ID NO 28
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 28
aaagactata aaakagcact tatatatatt ttccattttt cttraakgat gmtraaaaga     60
tgttaatcta gttgagrtgt tcrtccrcac tactcttaty tcaycatcct tagtattttg    120
ttaaaaaaaa aaraaaaaak awtcttcatt tttaactctt tgatgatst agtaattggt    180 attgtaaaat gttcttgaaa t                                               201

<210> SEQ ID NO 29
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 29
ttttaactct tttcccctgt gtatgtatgt acttgcagtt taatagatga acgtagctta     60
gaagtgatag catttgcatc tttactctta cggccatttc awtttctgaa actgaaagat    120
taaaacaaag atggcyatca atttctaatt taccttgcct tcaaagattt ggwactgctt    180
aattctttct tgaaattctc t                                               201
```

```
<210> SEQ ID NO 30
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 30
ttttaactct tttcccctgt gtatgtatgt acttgcagtt taatagatga acgtagctta      60
gaagtgatag catttgcatc tttactctta cggccatttc cwtttctgaa actgaaagat     120
taaaacaaag atggcyatca atttctaatt taccttgcct tcaaagattt ggwactgctt     180
aattctttct tgaaattctc t                                                201

<210> SEQ ID NO 31
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 31
aaacttatay gatttttaca atttctataa ctattgtaag tttaagaatc caattttaat      60
acttgcayaa atttgagrac tcaattttta yaattgaaac aattgagagt tcraagatat     120
aattgcaayt mctatkgtac tttaaggtgr tttttrcaar ttttcyttaa agrtaaatra     180
akattttatc tacttyattg c                                                201

<210> SEQ ID NO 32
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 32
aaacttatay gatttttaca atttctataa ctattgtaag tttaagaatc caattttaat      60
acttgcayaa atttgagrac tcaattttta yaattgaaac tattgagagt tcraagatat     120
aattgcaayt mctatkgtac tttaaggtgr tttttrcaar ttttcyttaa agrtaaatra     180
akattttatc tacttyattg c                                                201

<210> SEQ ID NO 33
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 33
ctcgaattga ttagatgata tttcgtgttr atgcgtcyat tgtgcacgac atcracgaga      60
ttaatctcta cgtgtcccaa tgattcctgt graaagatc attttgaaca atttcgaacc     120
```

```
gattcgtaag caagagggga amaaatttgt gatgtgatgt gatgtgatgt tacctttgag    180
aggaaactga aaaggctgct c                                              201
```

<210> SEQ ID NO 34
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 34

```
ctcgaattga ttagatgata tttcgtgttr atgcgtcyat tgtgcacgac atcracgaga    60
ttaatctcta cgtgtcccaa tgattcctgt graaaagatc gttttgaaca atttcgaacc    120
gattcgtaag caagagggga amaaatttgt gatgtgatgt gatgtgatgt tacctttgag    180
aggaaactga aaaggctgct c                                              201
```

<210> SEQ ID NO 35
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 35

```
gatgtttcgc caggagaaga attmgataag gttttttcag ctatttctka tggaaaattg    60
atagatscaa tgcttgaatg tttgaargat tggaatggtg ttccscttcc tcttagttag    120
attgtgttgt tttmtgttgt gtccatacaa ggaycaagt tacktttcta aacccatata    180
ttyttttaat gtatacattt c                                              201
```

<210> SEQ ID NO 36
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 36

```
gatgtttcgc caggagaaga attmgataag gttttttcag ctatttctka tggaaaattg    60
atagatscaa tgcttgaatg tttgaargat tggaatggtg ctccscttcc tcttagttag    120
attgtgttgt tttmtgttgt gtccatacaa ggaycaagt tacktttcta aacccatata    180
ttyttttaat gtatacattt c                                              201
```

<210> SEQ ID NO 37
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 37

```
ttttactagt ttggaargat gttttttycrr attctattaa cctytcwttc ttgccgatra      60
aatttgggaa taatgaattt tggtcgtttg ttattatttt tttttttaca atatatgggr     120
tggggagttg aacctttgac ttaagattga taatacaaac atratgtcag ttaaggtatg     180
ctcgttttgg tttgatcgtt g                                               201
```

<210> SEQ ID NO 38
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 38

```
ttttactagt ttggaargat gttttttycrr attctattaa cctytcwttc ttgccgatra      60
aatttgggaa taatgaattt tggtcgtttg ttattatttt tttttttaca atatatgggr     120
tggggagttg aacctttgac ttaagattga taatacaaac atratgtcag ttaaggtatg     180
ctcgttttgg tttgatcgtt g                                               201
```

<210> SEQ ID NO 39
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 39

```
gcrwagctta attggtaagg acacaagata ttcacrtttc tatatattgg ttagataktt      60
ttcayttttg ggtgatataa gccctactca araggatctc ctaycaattg aagtagctaa     120
ttgtatmtta acttatatag atagctatga tcttccattt gttttagytc gcttcagact     180
ttggtcgcac tctcaakatt a                                               201
```

<210> SEQ ID NO 40
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 40

```
gcrwagctta attggtaagg acacaagata ttcacrtttc tatatattgg ttagataktt      60
ttcayttttg ggtgatataa gccctactca araggatctc ataycaattg aagtagctaa     120
ttgtatmtta acttatatag atagctatga tcttccattt gttttagytc gcttcagact     180
ttggtcgcac tctcaakatt a                                               201
```

<210> SEQ ID NO 41
<211> LENGTH: 201
<212> TYPE: DNA
<213> ORGANISM: Citrullus lanatus
<220> FEATURE:
<221> NAME/KEY: source

```
<222> LOCATION: 1..201
<223> OTHER INFORMATION: /organism="Citrullus lanatus"
      /mol_type="unassigned DNA"

<400> SEQUENCE: 41
ttagtggtcg aataactgtg agaaccaaaa cagttatttt ctataaagtt tacagactaa      60
aagagaaact tgaaagttca tccaccaaaa tagattaaag gttaaaattg tagacgccaa     120
aaaatacagt ttttttaat gttcaagaat caaaatcgaa tgatcttaga agtttgtgga     180
ctaaaaagat gagtttctc a                                                 201

<210> SEQ ID NO 42
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 42
ttagtggtcg aataactgtg agaaccaaaa cagttatttt ctataaagtt tacagactaa      60
aagagaaact tgaaagttca tccaccaaaa tagattaaag cttaaaattg tagacgccaa     120
aaaatacagt ttttttaat gttcaagaat caaaatcgaa tgatcttaga agtttgtgga     180
ctaaaaagat gagtttctc a                                                 201

<210> SEQ ID NO 43
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 43
tgatcatctg cagctcacca aagtcctcat gggattccat ctagaatatg aatcaatcgt      60
gttgccttat tacaccgcaa tcctttgtca tgtctagatg tagcaatcca agaaattttg     120
tttgaggaga aaagacttgg catagtctcc ttcctatcat ctgatgttgc tctcatgacc     180
attcattcac gacctgcaaa t                                                201

<210> SEQ ID NO 44
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 44
tgatcatctg cagctcacca aagtcctcat gggattccat ctagaatatg aatcaatcgt      60
gttgccttat tacaccgcaa tcctttgtca tgtctagatg cagcaatcca agaaattttg     120
tttgaggaga aaagacttgg catagtctcc ttcctatcat ctgatgttgc tctcatgacc     180
attcattcac gacctgcaaa t                                                201

<210> SEQ ID NO 45
```

```
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 45
acttcccgtt taaggcacca aatataatgg tgaatataat tatttataac cttactattt      60
caaaatccta tttactacgg tatttattat ttttcactta cctatctctt tttttctttg     120
cgatagagtt actatttcct acctaaacaa aagtagttta cactccaaac atatactatt    180
ataatcagat taaaatagtt t                                               201

<210> SEQ ID NO 46
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 46
acttcccgtt taaggcacca aatataatgg tgaatataat tatttataac cttactattt      60
caaaatccta tttactacgg tatttattat ttttcactta tctatctctt tttttctttg     120
cgatagagtt actatttcct acctaaacaa aagtagttta cactccaaac atatactatt    180
ataatcagat taaaatagtt t                                               201

<210> SEQ ID NO 47
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 47
taatagtaat gtcraaytga rtagggtaat attgtgcagc ttaaatgaga aatgatttyc      60
ctatttataa attrgtgtca tggtcatgta taccttaagt cgrcctaaat catgaaggaa    120
atatctcrtg gtcacmtarg aaagcctact ttagttatta aatcttctay atagttgaga    180
gttgtaaatg atgttattca c                                               201

<210> SEQ ID NO 48
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 48
taatagtaat gtcraaytga rtagggtaat attgtgcagc ttaaatgaga aatgatttyc      60
ctatttataa attrgtgtca tggtcatgta taccttaagt tgrcctaaat catgaaggaa    120
atatctcrtg gtcacmtarg aaagcctact ttagttatta aatcttctay atagttgaga    180
```
gttgtaaatg atgttattca c                                                   201

<210> SEQ ID NO 49
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 49
tccaaaacta ttatcttctt tggtcaaata tctgataaat gacattaaat acagaaggca         60
agaaaacaac tcgagaagca attctacaat taactgtaac aatattgata catggactaa        120
tttctcctat gcctaactga acctttycca tctcaagaat aacttaccaa taamtatgag        180
atcgratact ctgaactcag g                                                   201

<210> SEQ ID NO 50
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 50
tccaaaacta ttatcttctt tggtcaaata tctgataaat gacattaaat acagaaggca         60
agaaaacaac tcgagaagca attctacaat taactgtaac tatattgata catggactaa        120
tttctcctat gcctaactga acctttycca tctcaagaat aacttaccaa taamtatgag        180
atcgratact ctgaactcag g                                                   201

<210> SEQ ID NO 51
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 51
accasgagcc atttaatttc yctmtcctta catttaatat aattggrtcy gtrtctaata         60
ttgggttgar gttttaagta atctatgagc catgaggttc aaaaaatatg ctatctcgag        120
ctatctcact ttatttatty gtggaaagaa ttctcgtggt tatggtaatg ttattttggg        180
tagattggac amttatattt t                                                   201

<210> SEQ ID NO 52
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 52
accasgagcc atttaatttc yctmtccttaa catttaatat aattggrtcy gtrtctaata    60
ttgggttgar gttttaagta atctatgagc catgaggttc gaaaaatatg ctatctcgag   120
ctatctcact ttatttatty gtggaaagaa ttctcgtggt tatggtaatg ttattttggg   180
tagattggac amttatattt t                                             201

<210> SEQ ID NO 53
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 53
gatcctttga atagatttct atttcctcgg tgagggaaga tctatctggt cttagagttg    60
aaaagttact agacgaaagt ggcgatgcag ttggagtacg tggagaagga gctagagaat   120
ttgcagcaga aatatctgtg gaaagttggg ggagaggagg aggtgatggt atggttgttt   180
ctgtgtagaa acttttattc t                                             201

<210> SEQ ID NO 54
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 54
gatcctttga atagatttct atttcctcgg tgagggaaga tctatctggt cttagagttg    60
aaaagttact agacgaaagt ggcgatgcag ttggagtacg gggagaagga gctagagaat   120
ttgcagcaga aatatctgtg gaaagttggg ggagaggagg aggtgatggt atggttgttt   180
ctgtgtagaa acttttattc t                                             201

<210> SEQ ID NO 55
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 55
ctcaaaatwa aaaaagtaa aagagaggtt agaaaaataa gttttaaaaa aagaagttac    60
ttttgtccct ccaaaacttts ttagtaaraa atamcaattt cctattagtt tttcctaart   120
gtgacaygat tgtcaagata agtctmytaa aaggaatcmg atctactaga acacaaaaaa   180
aattgatcta ttttcctaaa t                                             201

<210> SEQ ID NO 56
<211> LENGTH: 201
<212> TYPE: DNA
<213> ORGANISM: Citrullus lanatus
<220> FEATURE:
<221> NAME/KEY: source
<222> LOCATION: 1..201

```
<223> OTHER INFORMATION: /organism="Citrullus lanatus"
     /mol_type="unassigned DNA"

<400> SEQUENCE: 56
ctcaaaatwa aaaaaagtaa aagagaggtt agaaaaataa gttttaaaaa aagaagttac      60
ttttgtccct ccaaaactts ttagtaaraa atamcaattt tctattagtt tttcctaart    120
gtgacaygat tgtcaagata agtctmytaa aaggaatcmg atctactaga acacaaaaaa    180
aattgatcta ttttcctaaa t                                              201

<210> SEQ ID NO 57
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
     /mol_type="unassigned DNA"

<400> SEQUENCE: 57
raagtttgaa gcctttagtt tctcattggt acccggcatg gtagcgtcct ggctttctgt      60
tttaaccatg aagttagaag tttcartgtt tgaaggtcca gcaryagtaa acgcactccc    120
ctgtgaaagt ttcatttgaa ttagatccaa caargacggg ctcttcctta gcacyaaacc    180
aagaggacta ggttcatcaa g                                              201

<210> SEQ ID NO 58
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
     /mol_type="unassigned DNA"

<400> SEQUENCE: 58
raagtttgaa gcctttagtt tctcattggt acccggcatg gtagcgtcct ggctttctgt      60
tttaaccatg aagttagaag tttcartgtt tgaaggtcca tcaryagtaa acgcactccc    120
ctgtgaaagt ttcatttgaa ttagatccaa caargacggg ctcttcctta gcacyaaacc    180
aagaggacta ggttcatcaa g                                              201

<210> SEQ ID NO 59
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
     /mol_type="unassigned DNA"

<400> SEQUENCE: 59
ttggatccta aaacttgtag aaattagacy cccaaattat aaaaattgaa ccctaaaact      60
tatacaactc ttacaatttc tataattta taagtttaag ggtycaattt taacactagt    120
gtaagtttaa tagaaaattt gaggttataa ttgcaactac aacactactt taaaggtaat    180
ttttrmaatt taccctcyt c                                               201

<210> SEQ ID NO 60
<211> LENGTH: 201
```

```
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 60
ttggatccta aaacttgtag aaattagacy cccaaattat aaaaattgaa ccctaaaact      60
tatacaactc ttacaatttc tataatttta taagtttaag agtycaattt taacactagt     120
gtaagtttaa tagaaaattt gaggttataa ttgcaactac aacactactt taaaggtaat    180
ttttrmaatt taccctcyt c                                                201

<210> SEQ ID NO 61
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 61
atcatgtcaa ttattgacca accaccattc gcagttctag aacagagaga caytaacaaa      60
gaatatattg gttttagttc atttcccaag ttgaatggam cttcaaacca acgtatrgta    120
ggcaatgctg aatgtcargt agaaaataaa acaattgaaa aatgtatgca ttggcattcc    180
ttcatatttc ttgttaaaaa c                                                201

<210> SEQ ID NO 62
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 62
atcatgtcaa ttattgacca accaccattc gcagttctag aacagagaga caytaacaaa      60
gaatatattg gttttagttc atttcccaag ttgaatggam attcaaacca acgtatrgta    120
ggcaatgctg aatgtcargt agaaaataaa acaattgaaa aatgtatgca ttggcattcc    180
ttcatatttc ttgttaaaaa c                                                201

<210> SEQ ID NO 63
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 63
aataaaaawa aawaattcat tatattattt gtgcatgtgt ttagccgttt atcatatata      60
atgatataat tttcattatt taataattac tatrtyaatt gagttatatt aagaattgtt    120
ccaagcaagg ttcaaaattc acgarcaarc tcaagtccaa agagaaagaa gagtctacat    180
```
aggrgttgcr tatcacaaaa t                                              201

<210> SEQ ID NO 64
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 64
aataaaaawa aawaattcat tatattattt gtgcatgtgt ttagccgttt atcatatata    60
atgatataat tttcattatt taataattac tatrtyaatt aagttatatt aagaattgtt   120
ccaagcaagg ttcaaaattc acgarcaarc tcaagtccaa agagaaagaa gagtctacat   180
aggrgttgcr tatcacaaaa t                                              201

<210> SEQ ID NO 65
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 65
taggctcccc taagttgaag aatccmttct caatcaacga accttaggat cyccctaasa    60
tcaagaatac cttcttgagt aacaayttaa tctccaatac gayctgatac aactcctyga   120
catcaacaac acttcctccr tcacaatttc taggattaac atagagatcc gatctttcgg   180
ccaccccrya racaaaatct c                                              201

<210> SEQ ID NO 66
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 66
taggctcccc taagttgaag aatccmttct caatcaacga accttaggat cyccctaasa    60
tcaagaatac cttcttgagt aacaayttaa tctccaatac aayctgatac aactcctyga   120
catcaacaac acttcctccr tcacaatttc taggattaac atagagatcc gatctttcgg   180
ccaccccrya racaaaatct c                                              201

<210> SEQ ID NO 67
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 67
ggaatggaga agccttcatc aatactcctt cactaccatc tgataaagca aaagtttctt    60

```
ttgaaaaagc taaagtaatt agattagatc gttacaattt ccttagttca aacaaatatt    120
tgtcctgttc agaatttaga atctaagggw aaaaaaaaaa aaaacttgtt tggatctaca    180
ttttatttga tccctaggtt t                                              201
```

<210> SEQ ID NO 68
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 68

```
ggaatggaga agccttcatc aatactcctt cactaccatc tgataaagca aaagtttctt    60
ttgaaaaagc taaagtaatt agattagatc gttacaattt acttagttca aacaaatatt    120
tgtcctgttc agaatttaga atctaagggw aaaaaaaaaa aaaacttgtt tggatctaca    180
ttttatttga tccctaggtt t                                              201
```

<210> SEQ ID NO 69
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 69

```
taaaactaat tttgggkgaa ttatatmaat tcaaatttat aagttaaaga tgccaattca    60
ctgatgatga aattacttaa tatatatatg acttttccca acctaagtac aacatrgttc    120
aattgggtca ggttgagtcc aaaacacacc cgtttgaact catataaaaa acccttagct    180
ttgaagtttg gatcctttca a                                              201
```

<210> SEQ ID NO 70
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 70

```
taaaactaat tttgggkgaa ttatatmaat tcaaatttat aagttaaaga tgccaattca    60
ctgatgatga aattacttaa tatatatatg acttttccca gcctaagtac aacatrgttc    120
aattgggtca ggttgagtcc aaaacacacc cgtttgaact catataaaaa acccttagct    180
ttgaagtttg gatcctttca a                                              201
```

<210> SEQ ID NO 71
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"

/mol_type="unassigned DNA"

<400> SEQUENCE: 71
tcagggaaag tgttcgcaca cataataaaa amactttaaa aatttaccct attttatcta 60
tatatctaag ctaataataa taatggtctk aaaaaatctc attttgttta gttttaacag 120
ttgtgcrtca actaattcac attttaaaga aatatrttag aattaataat tatgaatttg 180
gaaaaagata rtaggtaaca a 201

<210> SEQ ID NO 72
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
       /mol_type="unassigned DNA"

<400> SEQUENCE: 72
tcagggaaag tgttcgcaca cataataaaa amactttaaa aatttaccct attttatcta 60
tatatctaag ctaataataa taatggtctk aaaaaatctc gttttgttta gttttaacag 120
ttgtgcrtca actaattcac attttaaaga aatatrttag aattaataat tatgaatttg 180
gaaaaagata rtaggtaaca a 201

<210> SEQ ID NO 73
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
       /mol_type="unassigned DNA"

<400> SEQUENCE: 73
gaagaaracg cattrccata tagattggga tttcctgagt aggtgttaat gatgaagagt 60
tctaacttct agactaagat ggagaactta tatatttaat tgttgtttgg gcttccagaa 120 cctttagga attattaatg gaaaacaagg rgacccaatg tccataaagg gatattggac 180
aacatattgg acmatgygta c 201

<210> SEQ ID NO 74
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
       /mol_type="unassigned DNA"

<400> SEQUENCE: 74
gaagaaracg cattrccata tagattggga tttcctgagt aggtgttaat gatgaagagt 60
tctaacttct agactaagat ggagaactta tatatttaat cgttgtttgg gcttccagaa 120 cctttagga attattaatg gaaaacaagg rgacccaatg tccataaagg gatattggac 180
aacatattgg acmatgygta c 201

<210> SEQ ID NO 75
<211> LENGTH: 201
<212> TYPE: DNA

```
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 75
gtagaagtat cttgatataa tatagatttg ggggtgtttt aataacttat gcttcaattt    60
tttagatttt gatttcaatt ttaattctat rttcttactt tgattttttt tggcastact   120
cctttcttrt cacatttcaa tctctattca caagtagaga tgtccrttra ayccgcggag   180
tcggggctct acrgggaccc g                                             201

<210> SEQ ID NO 76
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 76
gtagaagtat cttgatataa tatagatttg ggggtgtttt aataacttat gcttcaattt    60
tttagatttt gatttcaatt ttaattctat rttcttactt ctgattttttt tggcastact  120 cctttcttrt cacatttcaa tctctattca caagtagaga tgtccrttra ayccgcggag   180
tcggggctct acrgggaccc g                                             201

<210> SEQ ID NO 77
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 77
gtcatgtcgt caatttcttt aatattgttg tgtctacgat tggaagcaaa tccagggttg    60
attaatgaat caagggtcat tttccgcttc tttcaatgat taattcgaat cgttgaaatt   120
tctggtgtta attattttc attgtgcaat gtaggtattg tgaaacggca aaatctgttt    180
tcaaggattt gcacaaagtt c                                             201

<210> SEQ ID NO 78
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 78
gtcatgtcgt caatttcttt aatattgttg tgtctacgat tggaagcaaa tccagggttg    60
attaatgaat caagggtcat tttccgcttc tttcaatgat gaattcgaat cgttgaaatt   120
tctggtgtta attattttc attgtgcaat gtaggtattg tgaaacggca aaatctgttt    180
tcaaggattt gcacaaagtt c                                             201
```

<210> SEQ ID NO 79
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 79
tatgttcaat gccaaacart aacaataagg raaaatgaag ggatctcatc mcaattaatc     60
tatatagaga agaaacattg gaagggtatt attgtaatta cgttagggct tatgaaaaac    120
tctgccagca ataagrgctg cttccatgac aaaggagatg acatcaatga catcatcaac    180
ttggcatttg ttccctttga a                                              201

<210> SEQ ID NO 80
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 80
tatgttcaat gccaaacart aacaataagg raaaatgaag ggatctcatc mcaattaatc     60
tatatagaga agaaacattg gaagggtatt attgtaatta agttagggct tatgaaaaac    120
tctgccagca ataagrgctg cttccatgac aaaggagatg acatcaatga catcatcaac    180
ttggcatttg ttccctttga a                                              201

<210> SEQ ID NO 81
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 81
aaaaayaaaa aacaaaaaac waaatggtta ccatacctaa akaascaact aattttaaaa     60
attaatctaa aacacatttt taacactcta tttataaaat taaaaaaayt ataattmtac    120
gtgtatarcc attctattac tttcttagtt atttaatttt ttttttttga gctatttaaa    180
acaaacattt taattgatkt a                                              201

<210> SEQ ID NO 82
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 82
aaaaayaaaa aacaaaaaac waaatggtta ccatacctaa akaascaact aattttaaaa     60
attaatctaa aacacatttt taacactcta tttataaaat aaaaaaaayt ataattmtac    120
gtgtatarcc attctattac tttcttagtt atttaatttt tttttttga gctatttaaa    180 acaaacattt taattgatkt a                                             201

<210> SEQ ID NO 83
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 83
tcratttcaa tggatatttc tggaaaaaat aaaaaattca aaaaataaag ttaaattagt     60
aaataaacat gtwatgattt ttaaaagtct attatttata tcatrtttac attagttaca    120
ttttgttgct tgcttttta tgyttcgtag attttctac ratacarttg aaatgtyrat    180
tcacctctcr tgtcgatrtc g                                             201

<210> SEQ ID NO 84
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 84
tcratttcaa tggatatttc tggaaaaaat aaaaaattca aaaaataaag ttaaattagt     60
aaataaacat gtwatgattt ttaaaagtct attatttata acatrtttac attagttaca    120
ttttgttgct tgcttttta tgyttcgtag attttctac ratacarttg aaatgtyrat    180
tcacctctcr tgtcgatrtc g                                             201

<210> SEQ ID NO 85
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 85
ctgcttcggt cggttttgac cggttttcgg tttaagttga tcactcctaa cttttagttc     60
tccaagacct tttcaattcc tctcacatcc aagatttcgt gtcgatattt tttttcaaa    120 tgtatttggg tactaaataa gttgatttgt tactaataat tcaacttggc atactatttt    180
tcactacatt aaagttattg a                                             201

<210> SEQ ID NO 86
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 86

| ctgcttcggt cggttttgac cggttttcgg tttaagttga tcactcctaa cttttagttc | 60 |
| tccaagacct tttcaattcc tctcacatcc aagatttcgt atcgatattt tttttcaaa | 120 |
| tgtatttggg tactaaataa gttgatttgt tactaataat tcaacttggc atactatttt | 180 |
| tcactacatt aaagttattg a | 201 |

<210> SEQ ID NO 87
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 87

| ttagcaagaa attaaatkaa gtyatctcct tatttgagag aaagagtaga attagaaaag | 60 |
| tgtgtacttt attccaatca cttctcatca ctataaatac taattctaaa tgttaaaaat | 120 |
| aacttagttt rtaacataaa atcracaaca aactcttttt aaacgtaact ccacaaaact | 180 |
| atccataatt acaaatatac r | 201 |

<210> SEQ ID NO 88
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 88

| ttagcaagaa attaaatkaa gtyatctcct tatttgagag aaagagtaga attagaaaag | 60 |
| tgtgtacttt attccaatca cttctcatca ctataaatac caattctaaa tgttaaaaat | 120 |
| aacttagttt rtaacataaa atcracaaca aactcttttt aaacgtaact ccacaaaact | 180 |
| atccataatt acaaatatac r | 201 |

<210> SEQ ID NO 89
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
    /mol_type="unassigned DNA"

<400> SEQUENCE: 89

| tatgttacac ccaatcttaa tttgcaatag gagcccaaag acgtgcatac atcctaaggg | 60 |
| aaagctttag gcagtaacat tcctcaaatg ttgacagtat cttggtctct ttctgtgatg | 120 |
| attttcataa aaagtgaatt gtctcttgga atctgggtta aaagggaata tctattgttc | 180 |
| acgtataaaa ctaatcaagg a | 201 |

<210> SEQ ID NO 90
<211> LENGTH: 201
<212> TYPE: DNA
<213> ORGANISM: Citrullus lanatus

```
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 90
tatgttacac ccaatcttaa tttgcaatag gagcccaaag acgtgcatac atcctaaggg    60
aaagctttag gcagtaacat tcctcaaatg ttgacagtat tttggtctct ttctgtgatg   120
attttcataa aaagtgaatt gtctcttgga atctgggtta aaagggaata tctattgttc   180
acgtataaaa ctaatcaagg a                                              201

<210> SEQ ID NO 91
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 91
atctgacctt ttaataggtg acatatattt aataagttga attatgttca agttggtgtt    60
aaacatttaa actaaggttt aatgcatttt agattctttg atgagaaata accattttaa   120
gtgaaaactt tcctttaaaa ttaactttct aattaaaaaa atctaaaaga attaatttca   180
tttagttgat tttaataatt t                                              201

<210> SEQ ID NO 92
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 92
atctgacctt ttaataggtg acatatattt aataagttga attatgttca agttggtgtt    60
aaacatttaa actaaggttt aatgcatttt agattctttg ctgagaaata accattttaa   120
gtgaaaactt tcctttaaaa ttaactttct aattaaaaaa atctaaaaga attaatttca   180
tttagttgat tttaataatt t                                              201

<210> SEQ ID NO 93
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 93
catttcaacc tctaagccaa taaaacatct tatttaacca aaaaatttta ttttgaaatg    60
aataaacaaa gcatctcgaa gactattaat ctcaactcta tcatcacccg ttatgatcat   120
gtcatcaaca tagagtagaa gtattatata ttttgaggtt gtcattgaaa cagacttaaa   180
tatgcatttg aagatttgaa a                                              201
```

<210> SEQ ID NO 94
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 94
catttcaacc tctaagccaa taaaacatct tatttaacca aaaaattttta ttttgaaatg      60 aataaacaaa gcatctcgaa gactattaat ctcaactcta ccatcacccg ttatgatcat     120
gtcatcaaca tagagtagaa gtattatata ttttgaggtt gtcattgaaa cagacttaaa     180
tatgcatttg aagatttgaa a                                                201

<210> SEQ ID NO 95
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 95
ctaatttcaa cctttccaaa ctatcaaaag ggattgacat gatattaata attaagatca      60
tatgctttaa gctactttgt ttggttggta aaaatgagat gcatttattc aatcaagtta     120
ttatattaat ttaatttcct tagtgggttt ggtttggtgc cttaaatatt tactaaccaa     180
aacccttatc aaattactgt c                                                201

<210> SEQ ID NO 96
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 96
ctaatttcaa cctttccaaa ctatcaaaag ggattgacat gatattaata attaagatca      60
tatgctttaa gctactttgt ttggttggta aaaatgagat tcatttattc aatcaagtta     120
ttatattaat ttaatttcct tagtgggttt ggtttggtgc cttaaatatt tactaaccaa     180
aacccttatc aaattactgt c                                                201

<210> SEQ ID NO 97
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 97
aacttcaatg ttctgaatct ggaaaaacta agtttaatgg accttagatg gtgaaaaaaa      60
aaaaaaaaaa aaaaaattca aaacatgcag ttggtttccg ccactgacaa atttcagacc     120

```
ttagaaaact gaagccaagc tcataaaata tttggaaaat aaatggtaca aacaatggtg      180
gagactcttc aactgagttt t                                                201

<210> SEQ ID NO 98
<211> LENGTH: 201
<212> TYPE: DNA
<213> ORGANISM: Citrullus lanatus
<220> FEATURE:
<221> NAME/KEY: source
<222> LOCATION: 1..201
<223> OTHER INFORMATION: /organism="Citrullus lanatus"
      /mol_type="unassigned DNA"

<400> SEQUENCE: 98
aacttcaatg ttctgaatct ggaaaaacta agtttaatgg accttagatg gtgaaaaaaa       60
aaaaaaaaaa aaaaaattca aaacatgcag ttggtttccg tcactgacaa atttcagacc      120
ttagaaaact gaagccaagc tcataaaata tttggaaaat aaatggtaca aacaatggtg      180
gagactcttc aactgagttt t                                                201
```